United States Patent
Hennessy et al.

(10) Patent No.: US 12,281,081 B2
(45) Date of Patent: Apr. 22, 2025

(54) HERBICIDAL COMPOUNDS

(71) Applicant: SYNGENTA CROP PROTECTION AG, Basel (CH)

(72) Inventors: Alan Joseph Hennessy, Bracknell (GB); Elizabeth Pearl Jones, Bracknell (GB); Suzanna Jane Dale, Bracknell (GB); Alexander William Gregory, Bracknell (GB); Ian Thomas Tinmouth Houlsby, Bracknell (GB); Yunas Bhonoah, Bracknell (GB); Julia Comas-Barcelo, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 887 days.

(21) Appl. No.: 17/429,516

(22) PCT Filed: Feb. 10, 2020

(86) PCT No.: PCT/EP2020/053349
§ 371 (c)(1),
(2) Date: Aug. 9, 2021

(87) PCT Pub. No.: WO2020/165102
PCT Pub. Date: Aug. 20, 2020

(65) Prior Publication Data
US 2022/0089543 A1    Mar. 24, 2022

(30) Foreign Application Priority Data
Feb. 11, 2019  (GB) ..................... 1901878

(51) Int. Cl.
| | | |
|---|---|---|
| *C07D 221/20* | (2006.01) | |
| *A01N 25/32* | (2006.01) | |
| *A01N 43/32* | (2006.01) | |
| *A01N 43/42* | (2006.01) | |
| *A01N 43/84* | (2006.01) | |
| *A01P 13/00* | (2006.01) | |

(52) U.S. Cl.
CPC .......... *C07D 221/20* (2013.01); *A01N 25/32* (2013.01); *A01N 43/42* (2013.01); *A01N 43/84* (2013.01); *A01P 13/00* (2021.08)

(58) Field of Classification Search
None
See application file for complete search history.

(56) References Cited

U.S. PATENT DOCUMENTS

| | | | |
|---|---|---|---|
| 11,980,188 B2 * | 5/2024 | Hennessy | A01N 25/02 |
| 2005/0054535 A1 | 3/2005 | Fischer et al. | |
| 2015/0342185 A1 * | 12/2015 | Mound | C07C 321/20 |
| | | | 549/417 |
| 2021/0047274 A1 * | 2/2021 | Hennessy | C07D 413/12 |
| 2021/0395196 A1 * | 12/2021 | Hennessy | C07D 413/06 |
| 2022/0267278 A1 * | 8/2022 | Hennessy | A01N 47/28 |

FOREIGN PATENT DOCUMENTS

| | | |
|---|---|---|
| WO | 2008110308 A2 | 9/2008 |
| WO | 2014096289 A2 | 6/2014 |
| WO | 2014191534 A1 | 12/2014 |
| WO | 2015197468 A1 | 12/2015 |

OTHER PUBLICATIONS

Koyanagi et al. ( Chapter 2: Bioisosterism in Agrochemicals, from Synthesis and Chemistry of Agrochemicals IV, Baker et al. ACS, 1995, p. 15-24).*
Reitz et al. (Exp. Opin. on Thera. Patents, 2009, 19(10), 1449-1453).*
Written Opinion of the International Authority and International Search Report for International Application No. PCT/EP2020/053349 mailed Apr. 14, 2020.

* cited by examiner

Primary Examiner — Erin E Hirt
(74) Attorney, Agent, or Firm — BakerHostetler; Toni-Junell Herbert

(57) ABSTRACT

The present invention relates to compounds of Formula (I), wherein R1, R2, R3, R4 and G are as defined herein. The invention further relates to herbicidal compositions which comprise a compound of Formula (I), to their use for controlling weeds, in particular in crops of useful plants.

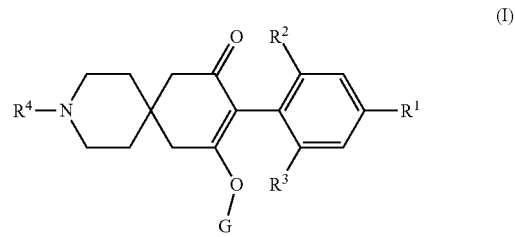

16 Claims, No Drawings

HERBICIDAL COMPOUNDS

CROSS-REFERENCE TO RELATED APPLICATIONS

This application is a 371 National Stage application of International Application No. PCT/EP2020/053349 filed Feb. 10, 2020, which claims priority to GB 1901878.7 filed Feb. 11, 2019, the entire contents of these applications are hereby incorporated by reference.

The present invention relates to novel herbicidal compounds, to processes for their preparation, to herbicidal compositions which comprise the novel compounds, and to their use for controlling weeds.

Herbicidal cyclic dione compounds substituted by a phenyl which has an alkynyl-containing substituent are disclosed in, for example, WO2014/096289 and WO2015/197468. The present invention relates to novel herbicidal cyclohexanedione derivatives with improved properties.

Thus, according to the present invention there is provided a compound of Formula (I)

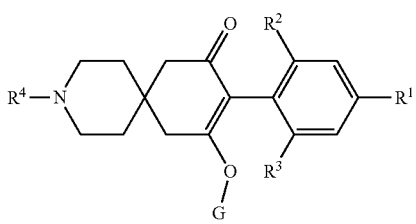

wherein
$R^1$ is selected from the group consisting of methyl, ethynyl, 1-propynyl, phenyl and a 5 or 6 membered heteroaryl which comprises one or two nitrogen heteroatoms, said phenyl and heteroaryl optionally substituted by one or two $R^9$ substituents;
$R^2$ is selected from the group consisting of methyl, ethyl, methoxy and chloro;
$R^3$ is selected from the group consisting of methyl, ethyl, methoxy and chloro;
$R^4$ is —S(O)$_2$NR$^5$R$^6$ or —S(O)(=NR$^7$)R$^8$;
$R^5$ is hydrogen or $C_1$-$C_6$alkyl; and
$R^6$ is selected from the group consisting of hydrogen, $C_1$-$C_6$alkyl, $C_3$-$C_6$cycloalkyl, $C_1$-$C_6$ alkoxy-$C_1$-$C_3$alkyl-, —C(O)C$_1$-$C_6$alkyl, —C(O)OC$_1$-$C_6$alkyl and CH$_2$CN; or
$R^5$ and $R^6$ together form —CH$_2$CH$_2$OCH$_2$CH$_2$—, —CH$_2$CH$_2$S(O)$_2$CH$_2$CH$_2$—; and
$R^7$ is hydrogen or $C_1$-$C_6$alkyl;
$R^8$ is selected from the group consisting of hydrogen, $C_1$-$C_6$ alkyl, $C_1$-$C_6$ alkoxy, $C_3$-$C_6$cycloalkyl, phenyl, -pyridyl, wherein the phenyl and pyridyl are optionally substituted by one, two or three substituents independently selected from the group consisting of $C_1$-$C_3$alkyl, $C_1$-$C_3$haloalkyl, $C_1$-$C_3$alkoxy, $C_2$-$C_3$alkenyl, $C_2$-$C_3$alkynyl, halogen, cyano and nitro;
$R^9$ is independently selected from the group consisting of $C_1$-$C_4$ alkyl, $C_1$-$C_4$ haloalkyl, cyano and halogen;
G is selected from the group consisting of hydrogen, —(CH$_2$)$_n$—R$^a$, —C(O)—R$^a$, —C(O)—(CR$^c$R$^d$)$_n$—O—R$^b$, —C(O)—(CR$^c$R$^d$)$_n$—S—R$^b$, —C(O)NR$^a$R$^a$, —S(O)$_2$—R$^a$ and $C_1$-$C_8$alkoxy-$C_1$-$C_3$alkyl-;

$R^a$ is independently selected from the group consisting of hydrogen, $C_1$-$C_8$alkyl, $C_1$-$C_3$haloalkyl, $C_2$-$C_8$alkenyl, $C_2$-$C_8$alkynyl, $C_3$-$C_6$cycloalkyl, heterocyclyl and phenyl wherein said heterocyclyl and phenyl groups are optionally substituted by one, two or three substituents independently selected from the group consisting of $C_1$-$C_3$alkyl, $C_1$-$C_3$haloalkyl, $C_1$-$C_3$alkoxy, $C_2$-$C_3$alkenyl, $C_2$-$C_3$alkynyl, halogen, cyano and nitro;
$R^b$ is selected from the group consisting of $C_1$-$C_8$alkyl, $C_1$-$C_3$haloalkyl, $C_2$-$C_8$alkenyl, $C_2$-$C_8$alkynyl, $C_3$-$C_6$ cycloalkyl, heterocyclyl and phenyl wherein said heterocyclyl and phenyl groups are optionally substituted by one, two or three substituents independently selected from the group consisting of $C_1$-$C_3$alkyl, $C_1$-$C_3$haloalkyl, $C_1$-$C_3$alkoxy, $C_2$-$C_3$alkenyl, $C_2$-$C_3$alkynyl, halogen, cyano and nitro;
$R^c$ is hydrogen or $C_1$-$C_3$ alkyl;
$R^d$ is hydrogen or $C_1$-$C_3$ alkyl; and
n is independently 0, 1 or 2;
or an agriculturally acceptable salt thereof.

Alkyl groups (e.g $C_1$-$C_6$alkyl) include, for example, methyl (Me, CH$_3$), ethyl (Et, C$_2$H$_5$), n-propyl (n-Pr), isopropyl (i-Pr), n-butyl (n-Bu), isobutyl (i-Bu), sec-butyl (s-Bu) and tert-butyl (t-Bu).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination.

Halogen (or halo) encompasses fluorine, chlorine, bromine or iodine. The same correspondingly applies to halogen in the context of other definitions, such as haloalkyl.

Haloalkyl groups (e.g $C_1$-$C_6$haloalkyl) are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups (e.g $C_1$-$C_4$alkoxy-) are, for example, methoxy, ethoxy, propoxy, isopropoxy, n-butoxy, isobutoxy, sec-butoxy or tert-butoxy, preferably methoxy and ethoxy.

Alkoxyalkyl groups (e.g $C_1$-$C_8$alkoxy-$C_1$-$C_3$alkyl-) includes, for example, methoxymethyl, methoxyethyl, ethoxymethyl, ethoxyethyl, n-propoxymethyl, n-propoxyethyl, isopropoxymethyl or isopropoxyethyl.

Cycloalkyl groups (e.g $C_3$-$C_6$cycloalkyl-) include, for example cyclopropyl (c-propyl, c-Pr), cyclobutyl (c-butyl, c-Bu), cyclopentyl (c-pentyl) and cyclohexyl (c-hexyl) and may be substituted or unsubstituted as indicated.

The invention also relates agriculturally acceptable salts of the compounds of Formula (I). Such salts include those which are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of Formula (I) according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

In one embodiment of the present invention in the Compound of Formula (I) $R^1$ is 1-propynyl, $R^2$ is methyl or methoxy and $R^3$ is methyl or methoxy.

In another embodiment of the present invention $R^1$ is phenyl optionally substituted by one or two $R^9$ substituents, e.g selected from the group consisting of cyano, chloro and fluoro.

In another embodiment of the present invention $R^1$ is a 5 or 6 membered heteroaryl which comprises one or two nitrogen heteroatoms, said heteroaryl optionally substituted by one or two $R^9$ substituents, e.g selected from the group consisting of cyano, chloro and fluoro. In a preferred embodiment, said heteroaryl is selected from the group consisting of pyridyl, pyrimidinyl, and pyrazolyl.

In one embodiment of the present invention $R^2$ is methoxy, chloro or methyl. In a preferred embodiment of the present invention $R^2$ is methyl.

In one embodiment of the present invention $R^3$ is methyl or methoxy, preferably methyl.

In one embodiment of the present invention $R^2$ is methyl and $R^3$ is methyl.

In one embodiment of the present invention $R^2$ is methyl and $R^3$ is methoxy.

In one embodiment of the present invention $R^2$ is methoxy and $R^3$ is methoxy.

In another embodiment of the present invention, $R^4$ is $C_1$-$C_2$alkoxy- (e.g methoxy or ethoxy).

In another embodiment of the present invention $R^4$ is —S(O)$_2$NR$^5$R$^6$. In this embodiment $R^5$ is preferably hydrogen or methyl and $R^6$ is preferably selected from the group consisting of methyl, ethyl, cyclopropyl, methoxyethyl-, —CH$_2$CN and CH$_3$C(O)—. More preferably, $R^6$ is methyl. In a more preferred embodiment, $R^5$ is hydrogen or methyl and $R^6$ is methyl. Alternatively, $R^5$ and $R^6$ may combine to form —CH$_2$CH$_2$OCH$_2$CH$_2$— or —CH$_2$CH$_2$S(O)$_2$CH$_2$CH$_2$—.

In another embodiment of the present invention $R^4$ is —S(O)(=NR$^7$)R$^8$. In this embodiment, $R^7$ is preferably hydrogen or methyl and $R^8$ is selected from the group consisting of $C_1$-$C_6$alkyl (preferably methyl or ethyl) and pyridyl.

In one embodiment of the present invention, G is selected from the group consisting of hydrogen, $C_1$-$C_8$alkyl (e.g methyl, ethyl, n-propyl, i-propyl, n-butyl, t-butyl, —C$_2$-C$_8$alkenyl (e.g vinyl), C$_2$-C$_8$alkynyl (e.g propargyl), —C(O)C$_1$-C$_8$alkyl (more preferably —C(O)C$_1$-C$_6$alkyl e.g —C(O)i-propyl and —C(O)t-butyl) and —C(O)—O—C$_1$-C$_8$alkyl (more preferably —C(O)—O—C$_1$-C$_6$alkyl e.g —C(O)—O-methyl). In a preferred embodiment, G is hydrogen.

Depending on the nature of the substituents, compounds of Formula (I) may exist in different isomeric forms. When G is hydrogen, for example, compounds of Formula (I) may exist in different tautomeric forms.

This invention covers all such isomers and tautomers and mixtures thereof in all proportions. Also, when substituents contain double bonds, cis- and trans-isomers can exist. These isomers, too, are within the scope of the claimed compounds of the Formula (I). Compounds of Formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula (I) and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The herbicidal compounds of present invention can also be used in mixture with one or more additional herbicides and/or plant growth regulators. Examples of such additional herbicides or plant growth regulators include acetochlor, acifluorfen (including acifluorfen-sodium), aclonifen, ametryn, amicarbazone, aminopyralid, aminotriazole, atrazine, bensulfuron (including bensulfuron-methyl), bentazone, bicyclopyrone, bilanafos, bispyribac-sodium, bixlozone, bromacil, bromoxynil, butachlor, butafenacil, carfentrazone (including carfentrazone-ethyl), cloransulam (including cloransulam-methyl), chlorimuron (including chlorimuron-ethyl), chlorotoluron, chlorsulfuron, cinmethylin, clacyfos, clethodim, clodinafop (including clodinafop-propargyl), clomazone, clopyralid, cyclopyranil, cyclopyrimorate, cyclosulfamuron, cyhalofop (including cyhalofop-butyl), 2,4-D (including the choline salt and 2-ethylhexyl ester thereof), 2,4-DB, desmedipham, dicamba (including the aluminium, aminopropyl, bis-aminopropylmethyl, choline, dichloroprop, diglycolamine, dimethylamine, dimethylammonium, potassium and sodium salts thereof) diclosulam, diflufenican, diflufenzopyr, dimethachlor, dimethenamid-P, diquat dibromide, diuron, ethalfluralin, ethofumesate, fenoxaprop (including fenoxaprop-P-ethyl), fenoxasulfone, fenquinotrione, fentrazamide, flazasulfuron, florasulam, florpyrauxifen (including florpyraxifen-benzyl), fluazifop (including fluazifop-P-butyl), flucarbazone (including flucarbazone-sodium), flufenacet, flumetsulam, flumioxazin, flupyrsulfuron (including flupyrsulfuron-methyl-sodium), fluroxypyr (including fluroxypyr-meptyl), fomesafen, foramsulfuron, glufosinate (including the ammonium salt thereof), glyphosate (including the diammonium, isopropylammonium and potassium salts thereof), halauxifen (including halauxifen-methyl), haloxyfop (including haloxyfop-methyl), hexazinone, hydantocidin, imazamox, imazapic, imazapyr, imazethapyr, indaziflam, iodosulfuron (including iodosulfuron-methyl-sodium), iofensulfuron (including iofensulfuron-sodium), ioxynil, isoproturon, isoxaflutole, lancotrione, MCPA, MCPB, mecoprop-P, mesosulfuron (including mesosulfuron-methyl), mesotrione, metamitron, metazachlor, methiozolin, metolachlor, metosulam, metribuzin, metsulfuron, napropamide, nicosulfuron, norflurazon, oxadiazon, oxasulfuron, oxyfluorfen, paraquat dichloride, pendimethalin, penoxsulam, phenmedipham, picloram, pinoxaden, pretilachlor, primisulfuron-methyl, propanil, propaquizafop, propyrisulfuron, propyzamide, prosulfocarb, prosulfuron, pyraclonil, pyraflufen (including pyraflufen-ethyl), pyrasulfotole, pyridate, pyriftalid, pyrimisulfan, pyroxasulfone, pyroxsulam, quinclorac, quinmerac, quizalofop (including quizalofop-P-ethyl and quizalofop-P-tefuryl), rimsulfuron, saflufenacil, sethoxydim, simazine, S-metalochlor, sulfentrazone, sulfosulfuron, tebuthiuron, tefuryltrione, tembotrione, terbuthylazine, terbutryn, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, triflusulfuron, 4-hydroxy-1-methoxy-5-methyl-3-[4-(trifluoromethyl)-2-pyridyl]imidazolidin-2-one, 4-hydroxy-1,5-dimethyl-3-[4-(trifluoromethyl)-2-pyridyl]imidazolidin-2-one, 5-ethoxy-4-hydroxy-1-methyl-3-[4-(trifluoromethyl)-2-pyridyl]imidazolidin-2-one, 4-hydroxy-1-methyl-3-[4-(trifluoromethyl)-2-pyridyl]imidazolidin-2-one, 4-hydroxy-1,5-dimethyl-3-[1-methyl-5-(trifluoromethyl)pyrazol-3-yl]imidazolidin-2-one, (4R)1-(5-tert-butylisoxazol-3-yl)-4-ethoxy-5-hydroxy-3-methyl-imidazolidin-2-one, 3-[2-(3,4-dimethoxyphenyl)-6-methyl-3-oxo-pyridazine-4-carbonyl]bicyclo[3.2.1]octane-2,4-dione, 2-[2-(3,4-dimethoxyphenyl)-6-methyl-3-oxo-pyridazine-4-carbonyl]-5-methyl-cyclohexane-1,3-dione, 2-[2-(3,4-dimethoxyphenyl)-6-methyl-3-oxo-pyridazine-4-carbonyl]cyclohexane-1,3-dione, 2-[2-(3,4-dimethoxyphenyl)-6-methyl-3-oxo-pyridazine-4-carbonyl]-5,5-dimethyl-cyclohexane-1,3-dione, 6-[2-(3,4-dimethoxyphenyl)-6-methyl-3-oxo-pyridazine-4-carbonyl]-2,2,4,4-tetramethyl-cyclohexane-1,3,5-trione, 2-[2-(3,4-dimethoxyphenyl)-6-methyl-3-oxo-pyridazine-4-carbonyl]-5-ethyl-cyclohexane-1,3-dione, 2-[2-(3,4-dimethoxyphenyl)-6-methyl-3-oxo-pyridazine-4-carbonyl]-4,4,6,6-tetramethyl-cyclohexane-1,3-dione, 2-[6-cyclopropyl-2-(3,4-dimethoxyphenyl)-3-oxo-pyridazine-4-carbonyl]-5-methyl-cyclohexane-1,3-dione, 3-[6-cyclopropyl-2-(3,4-dimethoxyphenyl)-3-oxo-pyridazine-4-carbonyl]bicyclo[3.2.1]octane-2,4-dione, 2-[6-cyclopropyl-2-(3,4-dimethoxyphenyl)-3-oxo-pyridazine-4-carbonyl]-5,5-dimethyl-cyclohexane-1,3-dione, 6-[6-cyclopropyl-2-(3,4-dimethoxyphenyl)-3-oxo-pyridazine-4-carbonyl]-2,2,4,4-tetramethyl-cyclohexane-1,3,5-trione, 2-[6-cyclopropyl-2-(3,4-dimethoxyphenyl)-3-oxo-pyridazine-4-carbonyl]cyclohexane-1,3-dione, 4-[2-(3,4-dimethoxyphenyl)-6-methyl-3-oxo-pyridazine-4-carbonyl]-2,2,6,6-tetramethyl-tetrahydropyran-3,5-dione and 4-[6-cyclopropyl-2-(3,4-dimethoxyphenyl)-3-oxo-pyridazine-4-carbonyl]-2,2,6,6-tetramethyl-tetrahydropyran-3,5-dione.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil.

Particularly preferred are mixtures of a compound of Formula (I) with cyprosulfamide, isoxadifen-ethyl, cloquintocet-mexyl and/or metcamifen.

The safeners of the compound of Formula (I) may also be in the form of esters or salts, as mentioned e.g. in The Pesticide Manual, 16$^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

The present invention still further provides a method of controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula (I) according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and Sorghum, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica,* Viola and *Xanthium*. The compounds of the present invention have been shown to exhibit particularly good activity against certain grass weed species, especially *Lolium Perenne*. Weeds can also include plants which may be considered crop plants but which are growing outside a crop area (escapes), or which grow from seed left over from a previous planting of a different crop (volunteers). Such volunteers or escapes may be tolerant to certain other herbicides.

The compounds of the present invention can be prepared according to the following schemes. Note that R$^1$ represents methyl with regard to the schemes provided in this section.

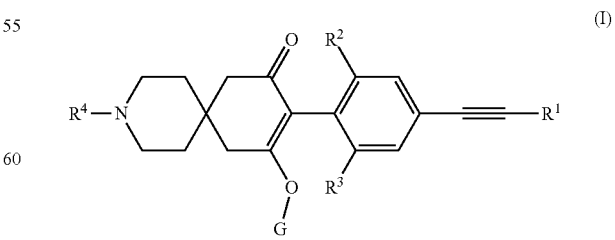

(I)

Compounds of formula (I) wherein G is other than hydrogen may be prepared by treating a compound of formula (I) wherein G is hydrogen, with a reagent G-Z, wherein G-Z is an alkylating agent such as an alkyl halide, acylating agent such as an acid chloride or anhydride, sulfonylating agent such as a sulfonyl chloride, carbamylating agent such as a carbamoyl chloride, or carbonating agent such as a chloroformate, using known methods.

Scheme 1

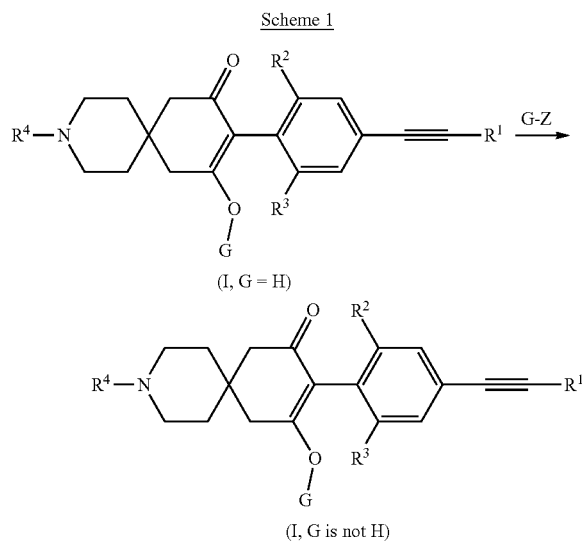

Compounds of formula (I) may be prepared by reacting an iodonium ylide of formula (A), wherein Ar is an optionally substituted phenyl group, and an aryl boronic acid of formula (B), in the presence of a suitable palladium catalyst, a base and in a suitable solvent.

Scheme 2

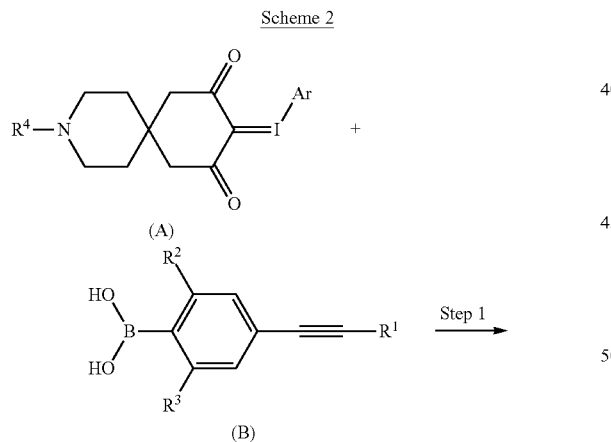

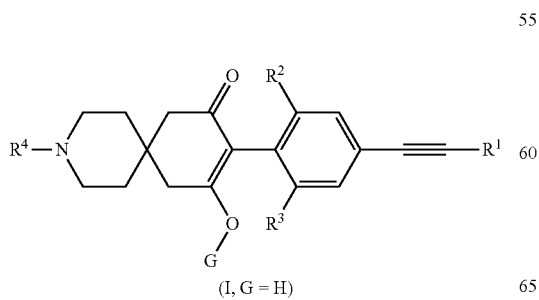

Suitable palladium catalysts are generally palladium(II) or palladium(0) complexes, for example palladium(II) dihalides, palladium(II) acetate, palladium(II) sulfate, bis(triphenylphosphine)-palladium(II) dichloride, bis(tricyclopentylphosphine)-palladium(I I) dichloride, bis(tricyclohexylphosphine)palladium(II) dichloride, bis(dibenzylideneacetone)palladium(0) or tetrakis-(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (N), the arylboronic acid of formula (O), and a base. Also suitable are bidendate ligands, for example 1,1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (N). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (A) may be prepared from a 1,3 dione compound of formula (C) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol using known procedures.

Scheme 3

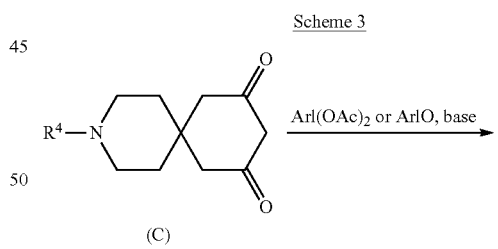

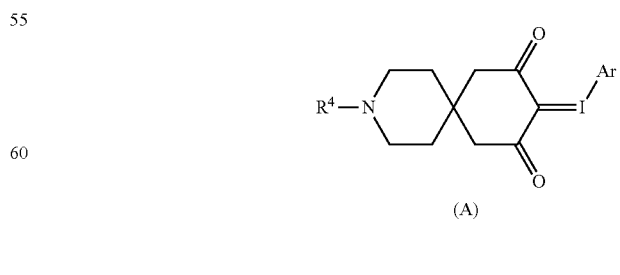

Alternatively, the propyne group may be added later in the synthetic sequence by decarboxylative propynylation such as in step 2 below.

Scheme 4

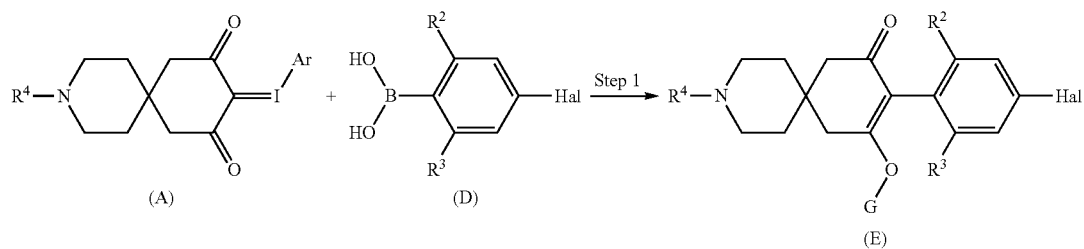

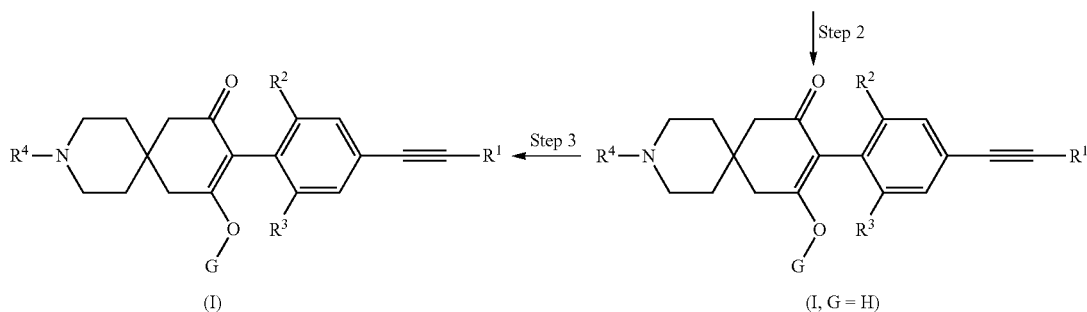

Boronic acids can be prepared by methods such as below in Scheme 5. For example, a compound of formula (B) or (D) may be prepared from an aryl halide of formula (F) or (H) by known methods. For example, an aryl halide of formula (F) or (H) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkyl borate (preferably trimethylborate) to give an aryl dialkylboronate which may be hydrolysed to provide a boronic acid of formula (B) or (D) under acidic conditions.

Scheme 5

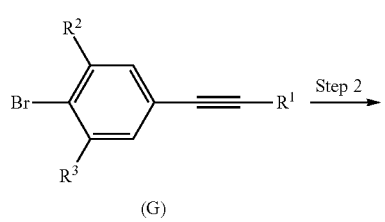

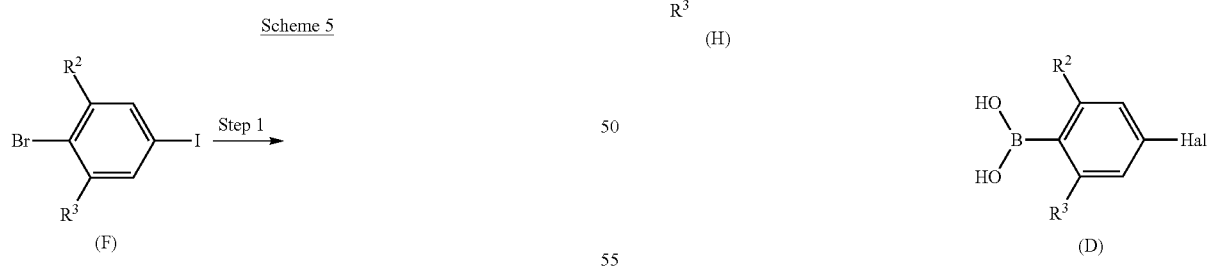

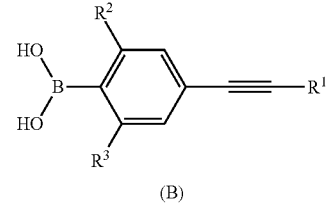

Compounds of formula (I) can also be prepared via Pb coupling as shown in the scheme below by reacting a compound of formula (D), to form an organolead reagent of formula (J) and subsequent reaction with 1,3 dione (C) under conditions described, for example, by J. Pinhey, Pure and Appl. Chem., (1996), 68 (4), 819 and by M. Moloney et al., Tetrahedron Lett., (2002), 43, 3407. A suitable triarylbismuth compound under conditions described, for example, by A. Yu. Fedorov et al., Russ. Chem. Bull. Int. Ed., (2005), 54 (11), 2602, and by P. Koech and M. Krische, J. Am. Chem. Soc., (2004), 126 (17), 5350 and references therein may be used as a related procedure.

Scheme 6

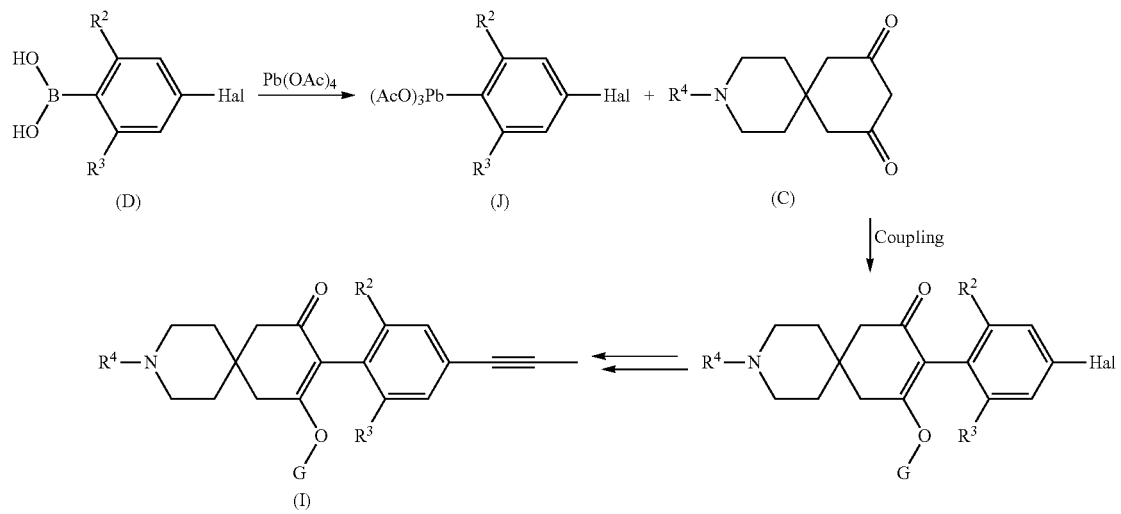

The compounds of type (I) can also be prepared via palladium coupling as shown in the scheme below, where boronic acid of type (B) is coupled to the suitably protected halo-alkene of type (K) in a Suzuki type coupling.

Scheme 7

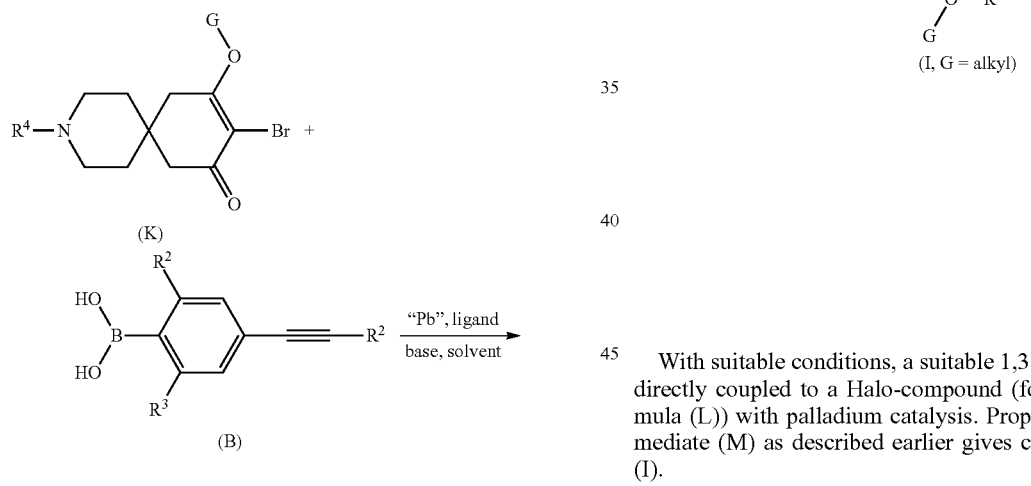

With suitable conditions, a suitable 1,3 dione may also be directly coupled to a Halo-compound (for example of formula (L)) with palladium catalysis. Propynylation of intermediate (M) as described earlier gives compounds of type (I).

Scheme 8

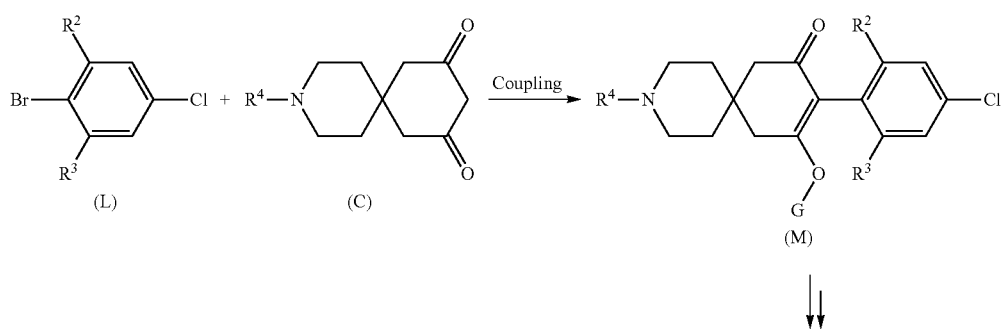

-continued

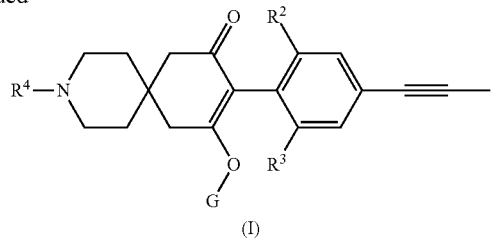

(I)

A compound of formula (I, G=H) may be prepared by the cyclisation of a compound of formula (N), wherein R is hydrogen or an alkyl group, preferably in the presence of an acid or base, and optionally in the presence of a suitable solvent, by analogous methods to those described by T. Wheeler, U.S. Pat. No. 4,209,532. The compounds of formula (N) have been particularly designed as intermediates in the synthesis of the compounds of the Formula (I). A compound of formula (N) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

Scheme 9

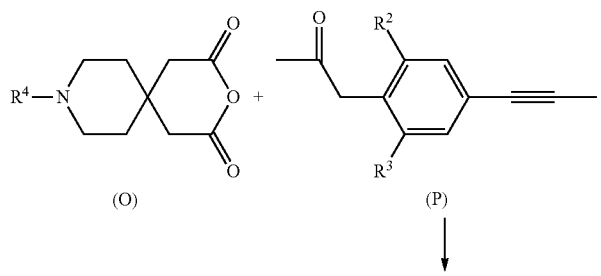

(O)    (P)

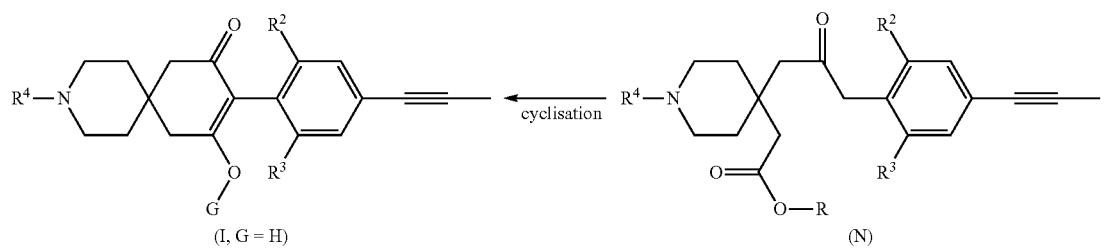

(I, G = H)    (N)

Compounds of type (I) can also be made by late stage functionalisation with use of a suitable protecting group as shown in the scheme below. Compound (Q) can be converted to intermediate (R) by the methods described and then the protecting group (such as the BOC group shown) can be removed (under acidic conditions in this example). Intermediate (S) can then be directly converted to compounds of type (T, G=H) by reacting with a suitable sulfamoyl chloride (in this example methyl sulfamoyl chloride). Compounds of type (T) can readily be converted to compounds of type (U, G is other than H) by the methods described earlier.

Scheme 10

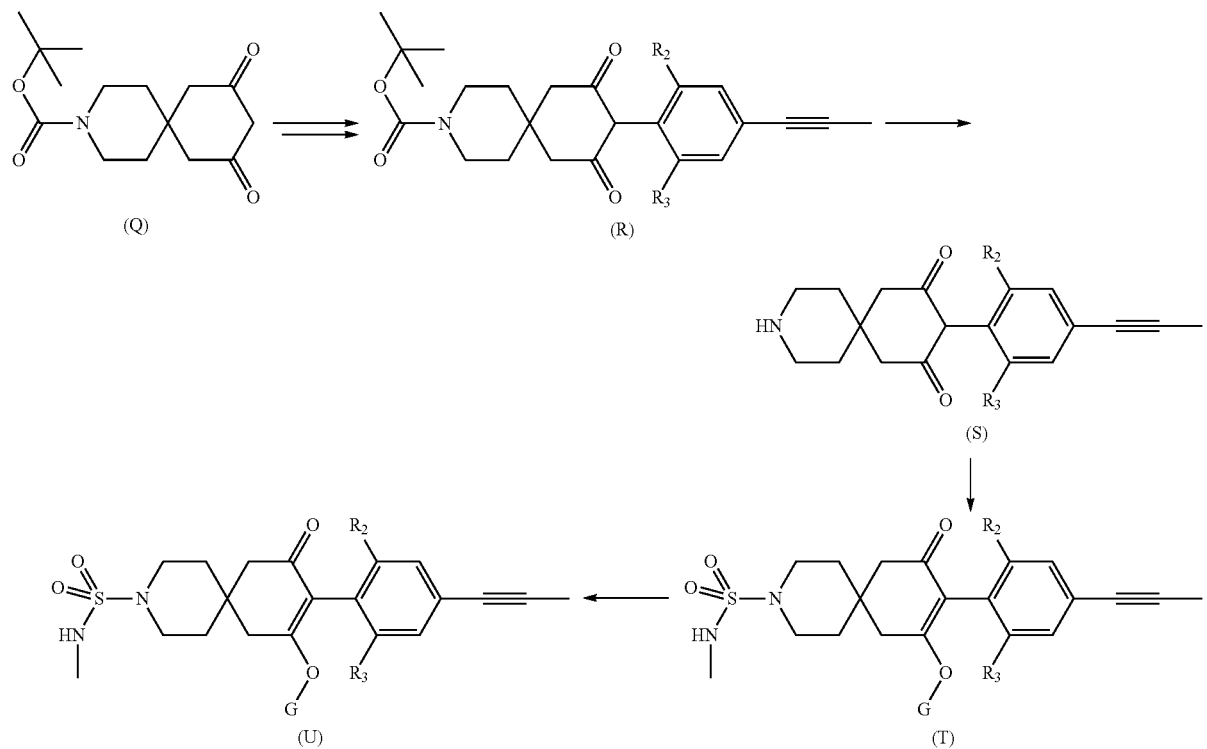

An intermediate of type (R) can be converted in enol ether of type (V, where G=alkyl) by the method described before and subsequent de-protection of the nitrogen protecting group (Such as the Boc group shown) can provide intermediate of type (O). Sulfonamidimides of type (Y) can be formed using the conditions described, for example, by Y. Chen, RSC Adv., (2015), 5, 4171 using a suitable silyl protected sulphonamide followed by acidic global deprotection (in this case TBS methyl sulphonamide). The formation of N-alkyl sulfonamidamides of type (AA) can be achieved by double alkylation of (Y) under basic conditions (in this case with iodomethane) to intermediates of type (Z) followed by acidic 0 dealkylation under standard conditions.

Scheme 11

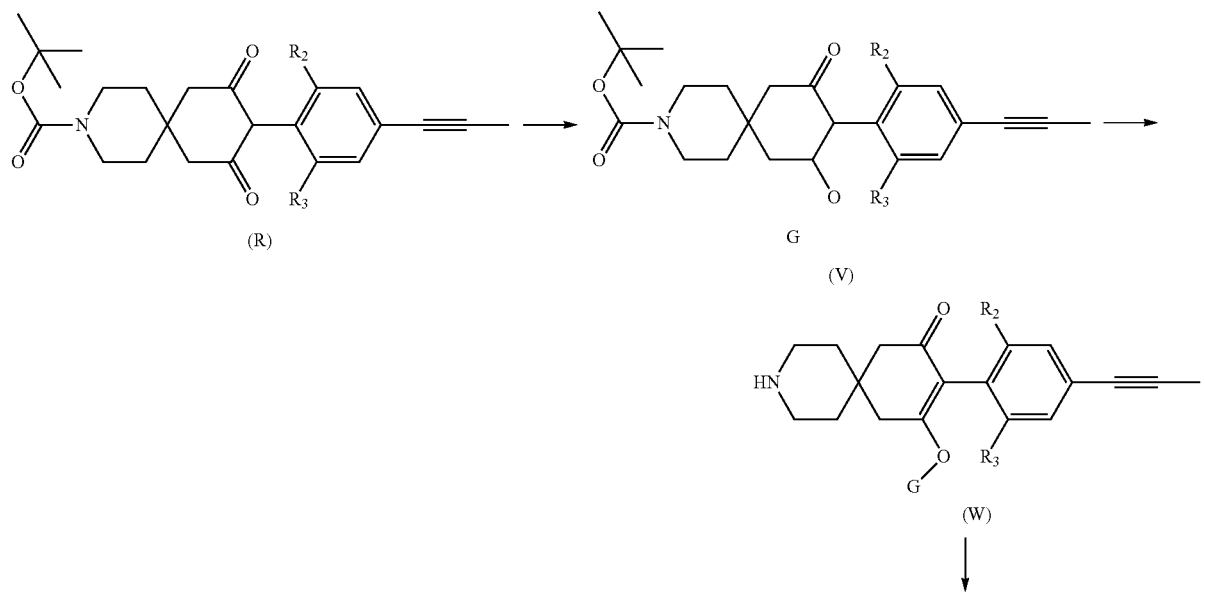

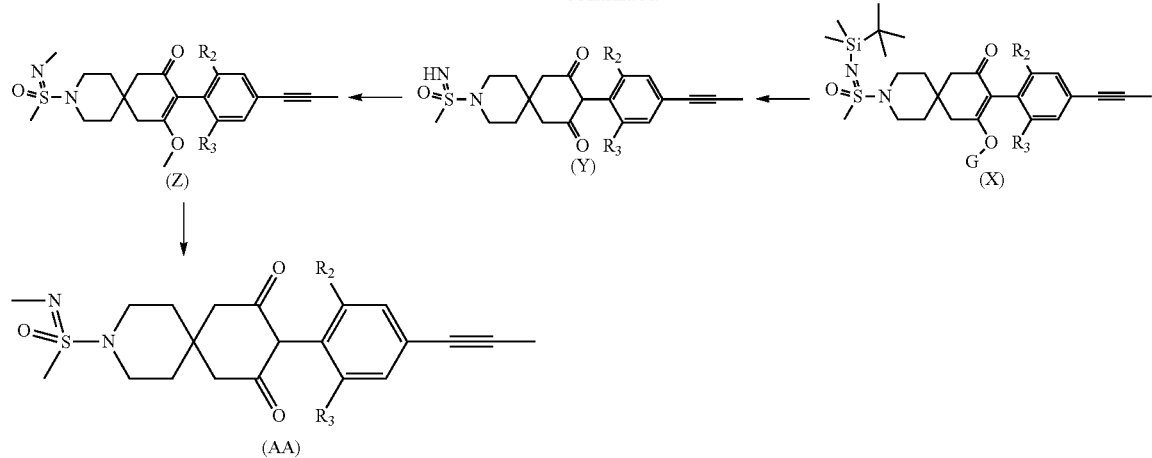

1,3 Diones such as these may be prepared using methods such as that shown below. So commercially available ketones (for example of type (AB)) can be converted into intermediate (AC) and then converted to intermediate (AD) and finally decarboxylation gives intermediate (Q) (these methods are described in WO2008/110308).

The following non-limiting examples provide specific synthesis methods for representative compounds of the present invention, as referred to in Tables 1 below.

EXAMPLE 1: SYNTHESIS OF 9-(2,6-DIMETHYL-4-PROP-1-YNYL-PHENYL)-3-(METHYLSULFONIMIDOYL)-3-AZASPIRO[5.5]UNDECANE-8,10-DIONE (COMPOUND A1)

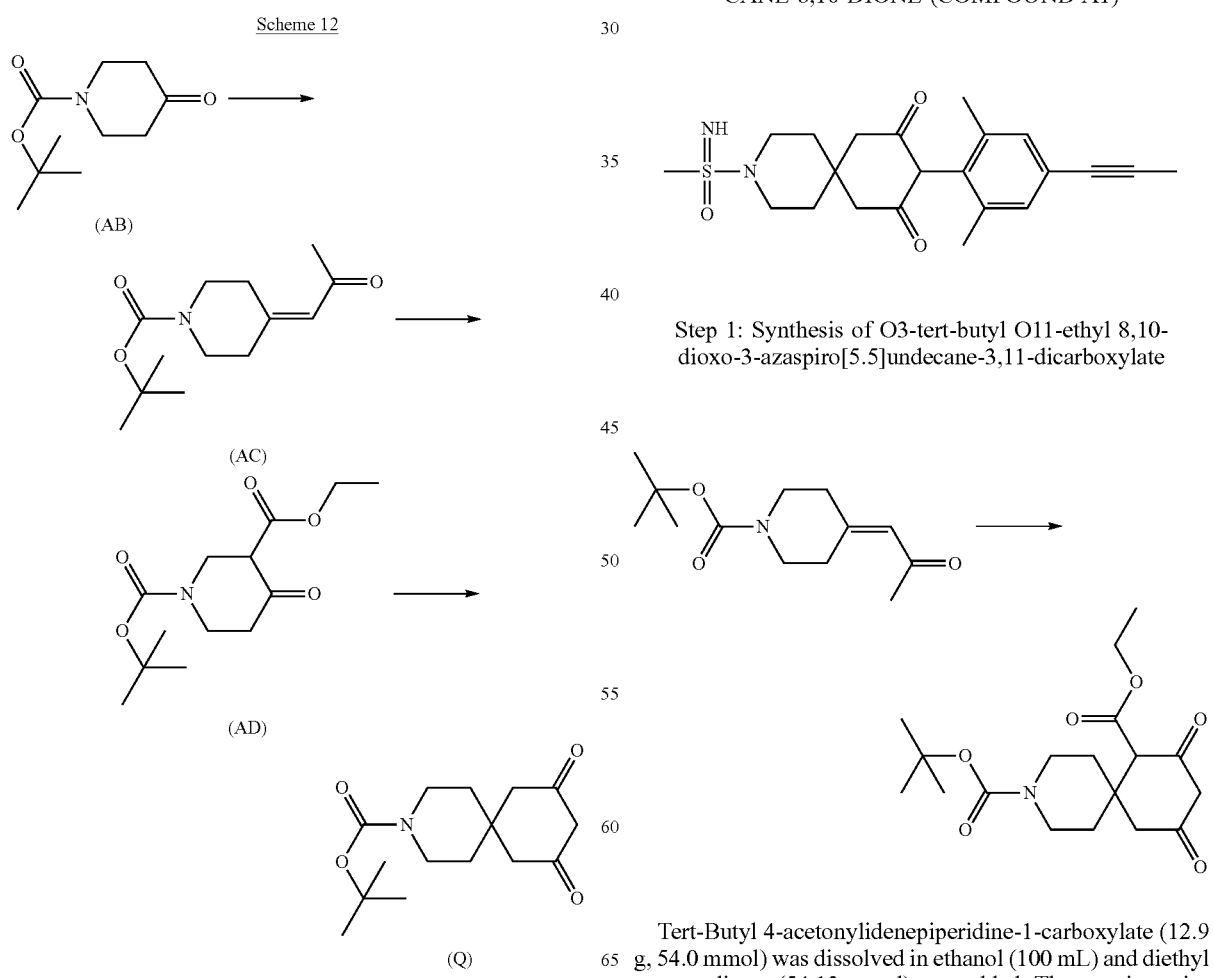

Step 1: Synthesis of O3-tert-butyl O11-ethyl 8,10-dioxo-3-azaspiro[5.5]undecane-3,11-dicarboxylate Tert-Butyl 4-acetonylidenepiperidine-1-carboxylate (12.9 g, 54.0 mmol) was dissolved in ethanol (100 mL) and diethyl propanedioate (54.12 mmol) was added. The reaction mixture was treated with a solution of sodium ethoxide which had been prepared by the addition of sodium (54.1 mmol) to ethanol (30 ml) at room temperature. The reaction mixture was stirred at room temperature for 3 hours then heated to reflux for 1 hour. Upon cooling the reaction mixture was concentrated in vacuo to give O3-tert-butyl O11-ethyl 8,10-dioxo-3-azaspiro[5.5]undecane-3,11-dicarboxylate as an oil, which was used in the next step without further purification.

Step 2: Synthesis of tert-butyl 8,10-dioxo-3-azaspiro[5.5]undecane-3-carboxylate

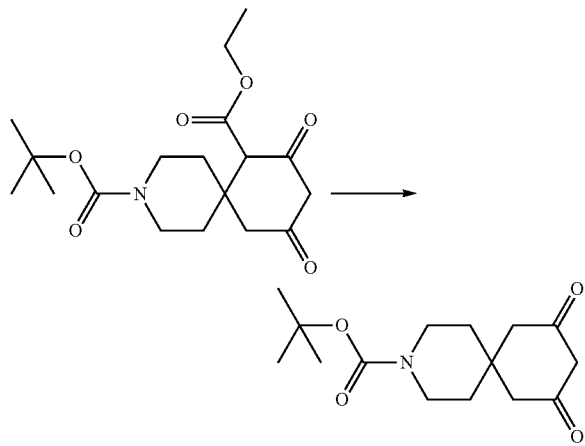

Crude O3-tert-butyl O11-ethyl 8,10-dioxo-3-azaspiro[5.5]undecane-3,11-dicarboxylate from step 1 was dissolved in aqueous NaOH (12M, 5 mL) and stirred for 5 hours. The reaction mixture was was acidified to pH 6 by the addition of conc HCl at 0° C., and extracted with EtOAc. The organics were dried and concentrated in vacuo to leave a yellow solid which on trituration yielded a pale pink powder of tert-butyl 8,10-dioxo-3-azaspiro[5.5]undecane-3-carboxylate. The aqueous layer was further acidified to pH 2 by the addition of conc HCl and extracted with EtOAc. The organics were dried and and concentrated in vacuo to leave a pale yellow solid which on trituration with ether gave a further batch of pale yellow powder of tert-butyl 8,10-dioxo-3-azaspiro[5.5]undecane-3-carboxylate (3.914 g, 13.91 mmol). 1H NMR (400 MHz, CDCl$_3$) 3.51-3.25 (m, 6H), 2.69-2.54 (m, 4H), 1.47-1.43 (m, 9H), 1.44-1.39 (m, 4H).

Step 3: Synthesis of tert-butyl 9-(4-bromo-2,6-dimethyl-phenyl)-8,10-dioxo-3-azaspiro[5.5]undecane-3-carboxylate

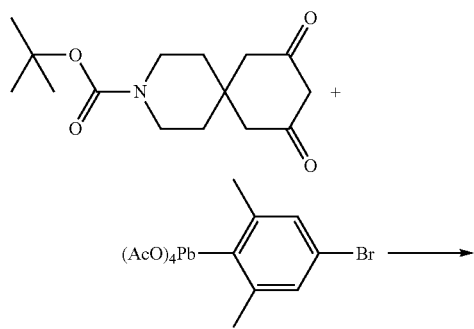

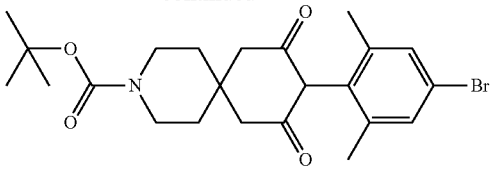

Tert-Butyl 8,10-dioxo-3-azaspiro[5.5]undecane-3-carboxylate (0.5 g, 1.8 mmol) and DMAP (1.1 g, 8.9 mmol) were dissolved in chloroform (20 mL). The reaction mixture was stirred under nitrogen for 10 minutes and toluene (5 mL) was added followed by [diacetoxy-(4-bromo-2,6-dimethyl-phenyl)plumbyl] acetate (1.2 g, 2.1 mmol). The resulting suspension was heated under nitrogen at 75° C. for 3 hours and then allowed to cool to room temperature. The reaction mixture was treated with 2 M HCl (50 mL) and white precipitate formed on stirring. The mixture was filtered and the organic phase was separated and the aqueous layer was extracted with DCM. The combined organics were dried (MgSO$_4$), evaporated and purified by flash column chromatography (gradient elution: 5-100% EtOAc:iso-hexane) to give tert-butyl 9-(4-bromo-2,6-dimethyl-phenyl)-8,10-dioxo-3-azaspiro[5.5]undecane-3-carboxylate (0.51 g, 1.1 mmol).

1H NMR (400 MHz, CD$_3$OD) 7.25-7.10 (m, 2H), 3.54-3.43 (m, 4H), 2.61-2.52 (m, 4H), 2.05-1.98 (m, 6H), 1.72-1.56 (m, 4H), 1.48-1.39 (m, 9H).

Step 4: Synthesis of tert-butyl 9-(2,6-dimethyl-4-prop-1-ynyl-phenyl)-8,10-dioxo-3-azaspiro[5.5]undecane-3-carboxylate (Compound A12)

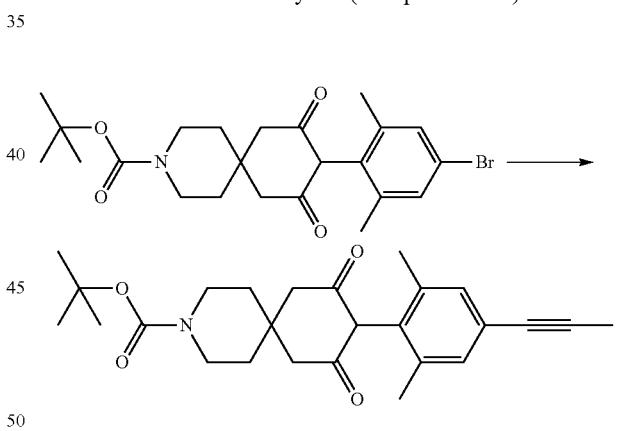

4-diphenylphosphanylbutyl(diphenyl)phosphane (32 mg, 0.075 mmol), dichlorobis(triphenylphosphine)palladium(II) (26 mg, 0.0373 mmol) and but-2-ynoic acid (346 mg, 0.894 mmol) were placed into a microwave vial. A solution of tert-butyl 9-(4-bromo-2,6-dimethyl-phenyl)-8,10-dioxo-3-azaspiro[5.5]undecane-3-carboxylate (0.346 g, 0.745 mmol) in DMSO (6 mL/mmol) was added followed by DBU (0.34 g, 2.24 mmol) and the reaction mixture was heated under microwave irradiation at 110° C. for 45 minutes. The reaction was diluted with 2M HCl and extracted with DCM. The organics were dried and concentrated in vacuo to leave an orange gum which purified by flash chromatography to give (gradient elution: 10-100% EtOAc in iso-hexane) tert-butyl 9-(2,6-dimethyl-4-prop-1-ynyl-phenyl)-8,10-dioxo-3-azaspiro[5.5]undecane-3-carboxylate (0.193 g, 0.456 mmol).

1H NMR (400 MHz, CD₃OD) 7.07-6.93 (m, 2H), 3.52-3.45 (m, 4H), 2.62-2.53 (m, 4H), 2.02-1.98 (m, 9H), 1.70-1.60 (m, 4H), 1.51-1.42 (m, 9H).

Step 5: Synthesis of tert-butyl 9-(2,6-dimethyl-4-prop-1-ynyl-phenyl)-8-methoxy-10-oxo-3-azaspiro[5.5]undec-8-ene-3-carboxylate

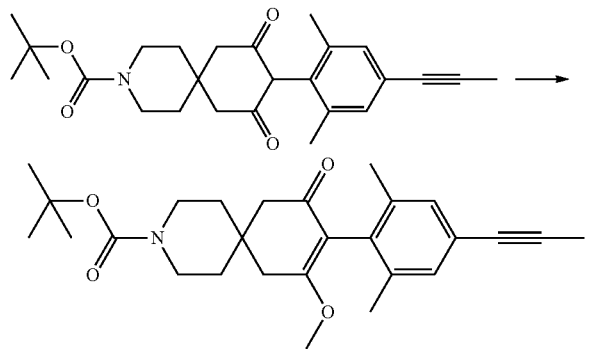

Tert-butyl 9-(2,6-dimethyl-4-prop-1-ynyl-phenyl)-8,10-dioxo-3-azaspiro[5.5]undecane-3-carboxylate (0.24 g, 0.56 mmol) was suspended in acetone (10 mL) at RT and then potassium carbonate (1.5 equiv., 0.83 mmol) was added followed by iodomethane (5 equiv., 2.77 mmol) and stirred at RT for 24 hours. The reaction mixture was concentrated in vacuo and then 2M HCl was added cautiously and the mixture extracted with EtOAc (×2). The combined organics were dried over sodium sulfate and concentrated in vacuo. The crude material was purified by flash column chromatography eluting with 5-100% EtOAc in iso-hexane to afford the title compound as an orange gum (0.18 g, 0.41 mmol, 74%).

¹H NMR (400 MHz, chloroform) δ=7.10-7.02 (m, 2H), 3.64-3.52 (m, 5H), 3.39-3.29 (m, 2H), 2.64-2.47 (m, 4H), 2.02-1.97 (m, 9H), 1.74-1.55 (m, 4H), 1.48-1.39 (m, 9H)

Step 6: Synthesis of 9-(2,6-dimethyl-4-prop-1-ynyl-phenyl)-8-methoxy-3-azaspiro[5.5]undec-8-en-10-one

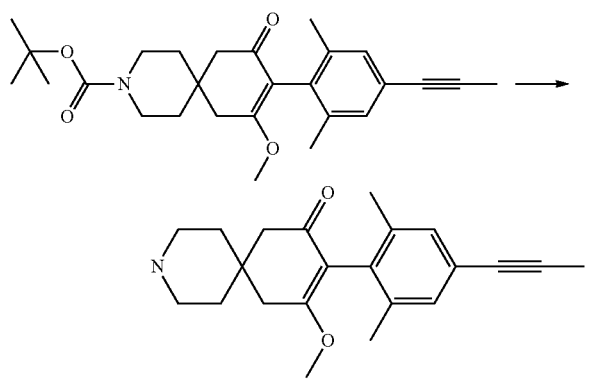

To a solution of tert-butyl 9-(2,6-dimethyl-4-prop-1-ynyl-phenyl)-8-methoxy-10-oxo-3-azaspiro[5.5]undec-8-ene-3-carboxylate (2.00 g, 4.57 mmol) in DCM (20 mL) at RT was added dropwise Hydrochloric Acid (HCl) (4M in Dioxane) (5.71 mL, 22.9 mmol). The resulting mixture was stirred at RT for 5 h before being evaporated under reduced pressure. The crude residue was diluted with ice-cold water (60 mL) and washed with DCM (20 mL). The aq layer was then rendered basic with 2M Na2CO3. The resulting solution was extracted with CHCl3:IPA (7:3, 3×20 mL). The combined organics were washed with brine and then passed through a phase-sep cartridge and the filtrate evaporated to afford 9-(2,6-dimethyl-4-prop-1-ynyl-phenyl)-8-methoxy-3-azaspiro[5.5]undec-8-en-10-one (1.40 g, 4.15 mmol, 90.8% Yield) as a pale yellow solid.

¹H NMR (400 MHz, methanol) δ ppm 1.71 (br t, J=5.50 Hz, 4H) 1.94-2.01 (m, 9H) 2.53 (s, 2H) 2.81 (s, 2H) 2.89 (br d, J=5.99 Hz, 4H) 3.75 (s, 3H) 7.00 (s, 2H).

Step 7: Synthesis of 3-[N-[tert-butyl(dimethyl)silyl]-S-methyl-sulfonimidoyl]-9-(2,6-dimethyl-4-prop-1-ynyl-phenyl)-8-methoxy-3-azaspiro[5.5]undec-8-en-10-one

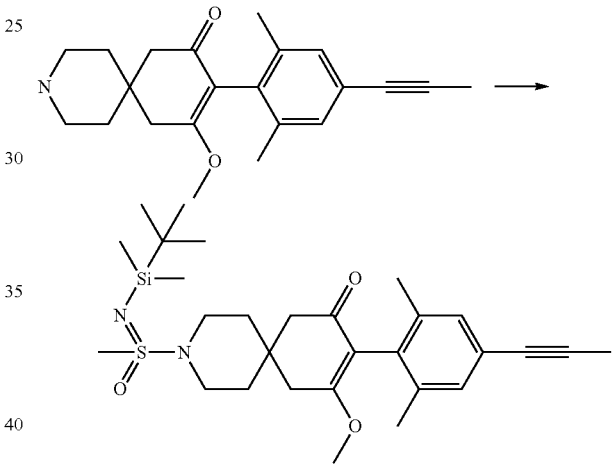

Triphenyl phosphine (0.34 g, 1.30 mmol) and hexachloroethane (0.31 g, 1.30 mmol) were suspended in chloroform (3 ml) and heated to 70° C. for 6 h. The mixture was cooled to rt, triethylamine (0.25 mL, 1.80 mmol) was added the mixture was stirred for 10 min at RT. The reaction mixture was cooled using an ice bath and N-[tert-butyl(dimethyl)silyl]methanesulfonamide (0.25 g, 1.20 mmol) was added in chloroform (1 ml). The reaction was stirred at 0° C. for 20 mins before 9-(2,6-dimethyl-4-prop-1-ynyl-phenyl)-8-methoxy-3-azaspiro[5.5]undec-8-en-10-one (0.27 g, 0.80 mmol) and triethylamine (0.25 mL, 1.80 mmol) were and added the reaction stirred at RT overnight. The reaction mixture was directly purified by flash column chromatography (EtOAc in Cyclohexane 0-100%) to give 3-[N-[tert-butyl(dimethyl)silyl]-S-methyl-sulfonimidoyl]-9-(2,6-dimethyl-4-prop-1-ynyl-phenyl)-8-methoxy-3-azaspiro[5.5]undec-8-en-10-one (220 mg, 0.42 mmol, 52%) as an off-white solid.

¹H NMR (400 MHz, methanol) δ=7.00 (s, 2H), 3.76 (s, 3H), 3.42-3.32 (m, 2H), 3.22-3.09 (m, 2H), 2.83-2.82 (m, 2H), 2.81 (s, 3H), 2.55 (s, 2H), 1.99 (d, J=1.6 Hz, 9H), 1.82 (t, J=5.6 Hz, 4H), 0.93-0.89 (m, 9H), 0.10 (s, 3H), 0.09 (s, 3H)

Step 8: Synthesis of 9-(2,6-dimethyl-4-prop-1-ynyl-phenyl)-3-(methylsulfonimidoyl)-3-azaspiro[5.5]undecane-8,10-dione (Compound A1)

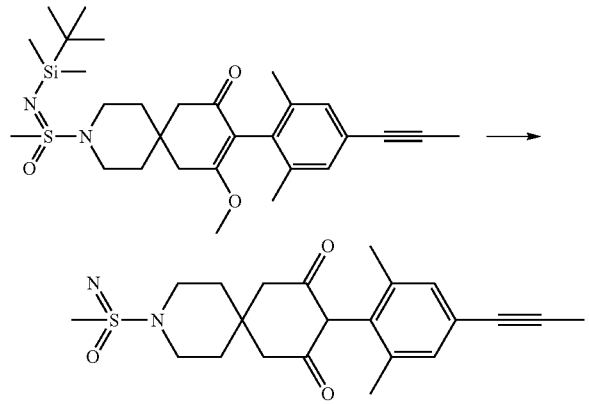

To a solution of 3-[N-[tert-butyl(dimethyl)silyl]-S-methyl-sulfonimidoyl]-9-(2,6-dimethyl-4-prop-1-ynyl-phenyl)-8-methoxy-3-azaspiro[5.5]undec-8-en-10-one (0.22 g, 0.418 mmol) in DCM (0.8 mL) at RT was added dropwise Hydrochloric Acid (HCl) (4M in Dioxane) (0.520 mL, 2.08 mmol). The resulting mixture was stirred at RT for 16 h. The mixture was extracted between DCM and H₂O and the organic phase was dried and concentrated in vacuo. Purification via flash column chromatography (EtOAc in Hexane 10-30%) gave 9-(2,6-dimethyl-4-prop-1-ynyl-phenyl)-3-(methylsulfonimidoyl)-3-azaspiro[5.5]undecane-8,10-dione (0.145 g, 87%) as an off-white solid.

¹H NMR (400 MHz, Methanol) δ=7.04 (s, 2H), 3.41-3.36 (m, 4H), 3.05 (s, 3H), 2.61 (s, 4H), 2.01 (s, 6H), 1.99 (s, 3H), 1.88-1.78 (m, 4H).

EXAMPLE 2: SYNTHESIS OF [9-(2,6-DIMETHYL-4-PROP-1-YNYL-PHENYL)-3-(METHYLSULFONIMIDOYL)-10-OXO-3-AZASPIRO[5.5]UNDEC-8-EN-8-YL] METHYL CARBONATE (COMPOUND P3)

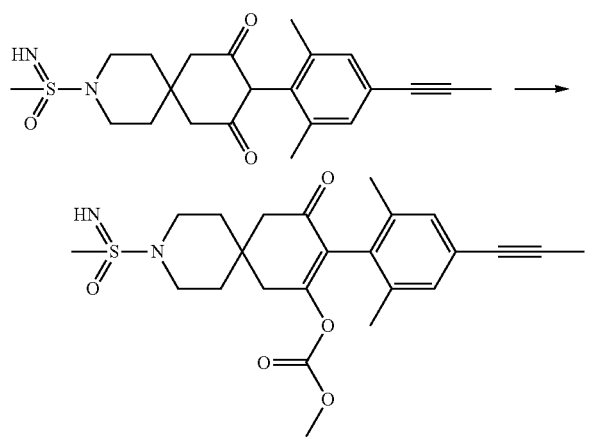

To a solution of 9-(2,6-dimethyl-4-prop-1-ynyl-phenyl)-3-(methylsulfonimidoyl)-3-azaspiro[5.5]undecane-8,10-dione (0.15 g, 0.37 mmol) in anhydrous DCM (3 mL) at RT was added triethylamine (0.16 mL, 1.12 mmol) and methyl chloroformate (0.044 mL, 0.56 mmol). The resulting mixture was stirred at RT for 1 h. The mixture was then diluted with DCM and washed with 10% aq citric acid and brine and then passed through a phase-sep cartridge and the filtrate evaporated. The crude residue was purified by flash chromatography (50-100% EtOAc in hexanes) to afford [9-(2,6-dimethyl-4-prop-1-ynyl-phenyl)-3-(methylsulfonimidoyl)-10-oxo-3-azaspiro[5.5]undec-8-en-8-yl] methyl carbonate (0.144 g, 0.314 mmol, 83.84% Yield) as a white solid.

1H NMR (400 MHz, CDCl₃) δ 7.08 (s, 2H), 3.69 (s, 3H), 3.41-3.27 (m, 4H), 2.83 (s, 3H), 2.77 (s, 2H), 2.62 (s, 2H), 2.03 (m, 9H), 1.93-1.75 (m, 4H)

EXAMPLE 3: SYNTHESIS OF 9-(2,6-DIMETHYL-4-PROP-1-YNYL-PHENYL)-N-METHYL-8,10-DIOXO-3-AZASPIRO[5.5]UNDECANE-3-SULFONAMIDE(COMPOUND A3)

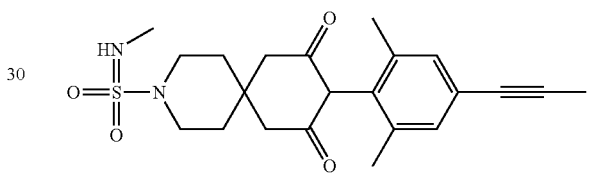

Step 1: Synthesis of 9-(2,6-dimethyl-4-prop-1-ynyl-phenyl)-3-azaspiro[5.5]undecane-8,10-dione Hydrochloride

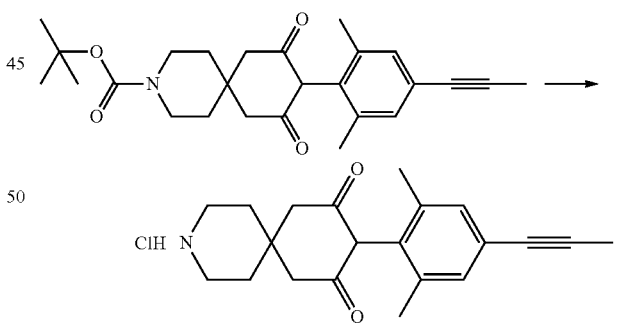

tert-Butyl 9-(2,6-dimethyl-4-prop-1-ynyl-phenyl)-8,10-dioxo-3-azaspiro[5.5]undecane-3-carboxylate (0.193 g, 0.456 mmol) was stirred for 1 hour at room temperature in 4 M HCl in 1,4-dioxane (4 mL, 16 mmol). The reaction mixture was concentrated in vacuo to leave 9-(2,6-dimethyl-4-prop-1-ynyl-phenyl)-3-azaspiro[5.5]undecane-8,10-dione hydrochloride as a white solid which was used directly in the next reaction without further purification.

Step 2: Synthesis of 9-(2,6-dimethyl-4-prop-1-ynyl-phenyl)-N-methyl-8,10-dioxo-3-azaspiro[5.5]undecane-3-sulfonamide(Compound A3)

EXAMPLE 4: SYNTHESIS OF [9-(2,6-DIMETHYL-4-PROP-1-YNYL-PHENYL)-3-(METHYLSULFAMOYL)-10-OXO-3-AZASPIRO[5.5]UNDEC-8-EN-8-YL] METHYL CARBONATE (COMPOUND P2)

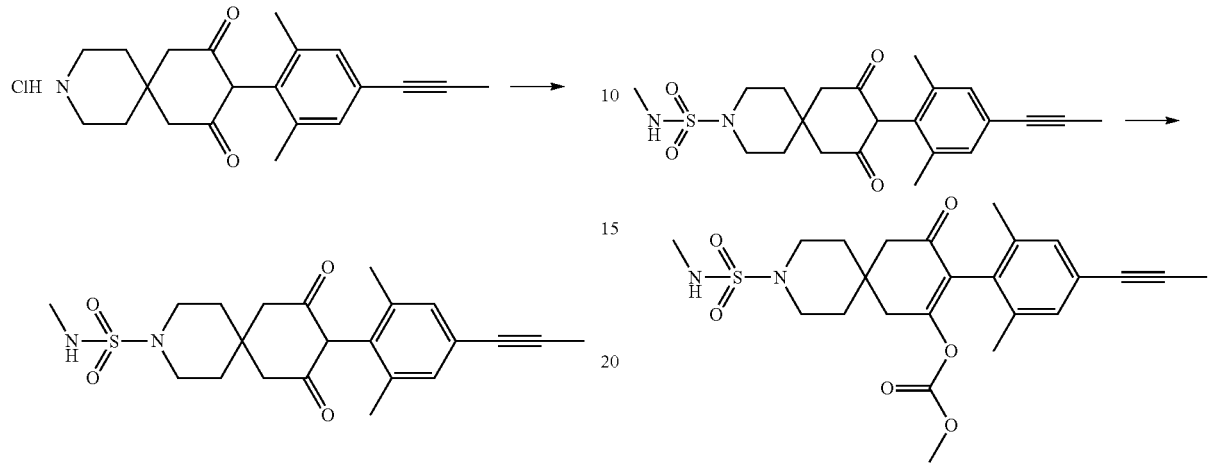

9-(2,6-dimethyl-4-prop-1-ynyl-phenyl)-3-azaspiro[5.5]undecane-8,10-dione;hydrochloride (0.20 g, 0.56 mmol) was taken up into DCM (5 mL). Triethylamine (0.22 mL, 1.58 mmol) was added and the reaction mixture was stirred for a few minutes at RT before N-methylsulfamoyl chloride (0.073 g, 0.567 mmol) was added and then stirred at room temperature for 2 hours. The reaction mixture was poured into 2M HCl and extracted with DCM (×2). The combined organics were dried over sodium sulfate and concentrated in vacuo. The residue was purified by flash column chromatography using a gradient from 5-100% EtOAc in iHex to give 9-(2,6-dimethyl-4-prop-1-ynyl-phenyl)-N-methyl-8,10-dioxo-3-azaspiro[5.5]undecane-3-sulfonamide (0.14 g, 0.34 mmol, 62%) as an off-white foam.

$^1$H NMR (400 MHz, Methanol) δ=7.06-7.00 (m, 2H), 3.67-3.61 (m, 1H), 3.28-3.17 (m, 4H), 2.66-2.62 (m, 3H), 2.60-2.52 (m, 4H), 2.02-1.96 (m, 9H), 1.80-1.74 (m, 4H)

9-(2,6-dimethyl-4-prop-1-ynyl-phenyl)-N-methyl-8,10-dioxo-3-azaspiro[5.5]undecane-3-sulfonamide (0.065 g, 0.16 mmol) was dissolved in dichloromethane (1.3 mL) then N,N-diethylethanamine (0.033 mL, 0.23 mmol) was added followed by methyl carbonochloridate (0.014 mL, 0.19 mmol). After stirring at room temperature for 2 hours the reaction mixture was concentrated in vacuo. The residue was purified by flash column chromatography, eluting with 5-100% EtOAc in iso-hexane to afford [9-(2,6-dimethyl-4-prop-1-ynyl-phenyl)-3-(methylsulfamoyl)-10-oxo-3-azaspiro[5.5]undec-8-en-8-yl] methyl carbonate (0.040 g, 0.084 mmol, 54%) as a white solid. $^1$H NMR (400 MHz, chloroform) δ=7.11-7.01 (m, 2H), 4.05-3.94 (m, 1H), 3.71-3.70 (m, 2H), 3.70-3.68 (m, 3H), 3.39-3.21 (m, 4H), 2.79-2.74 (m, 4H), 2.04-2.01 (m, 9H), 1.91-1.71 (m, 4H)

Examples of herbicidal compounds of the present invention.

TABLE 1

| Compound | Structure | NMR |
|---|---|---|
| A1 | 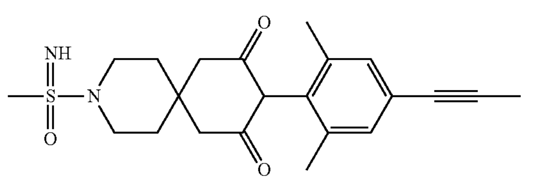 [SMILES: CC#Cc1cc(C)c(C2C(=O)CC3(CCN(S(C)(=N)=O)CC3)CC2=O)c(C)c1] | 1H NMR (400 MHz, Methanol-d4) δ = 7.13-6.97 (m, 2H), 3.31 (br s, 4H), 3.08-2.97 (m, 3H), 2.69-2.54 (m, 4H), 2.09-1.95 (m, 9H), 1.89-1.77 (m, 4H). |
| A2 | 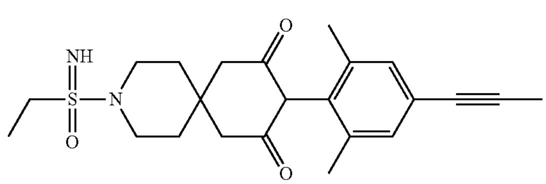 [SMILES: CC#Cc1cc(C)c(C2C(=O)CC3(CCN(S(=N)(=O)CC)CC3)CC2=O)c(C)c1] | 1H NMR (400 MHz, Methanol-d4) δ = 7.06-7.01 (m, 2H), 3.45-3.35 (m, 4H), 3.12 (d, J = 7.3 Hz, 2H), 2.60 (s, 4H), 2.01 (s, 6H), 1.99 (s, 3H), 1.79 (t, J = 5.6 Hz, 4H), 1.36 (t, J = 7.3 Hz, 3H). |

TABLE 1-continued

| Compound | Structure | NMR |
|---|---|---|
| A3 | 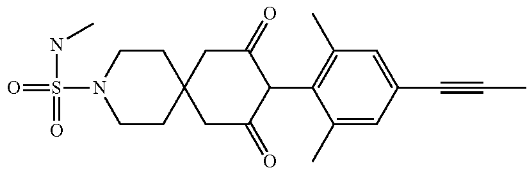 | 1H NMR (400 MHz, Methanol-d4) δ = 7.06-7.00 (m, 2H), 3.67-3.61 (m, 1H), 3.28-3.17 (m, 4H), 2.66-2.62 (m, 3H), 2.60-2.52 (m, 4H), 2.02-1.96(m, 9H), 1.80-1.74 (m, 4H) |
| A4 | 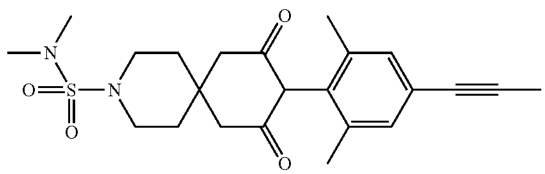 [SMILES: CC#Cc1cc(C)c(C2C(=O)CC3(CCN(S(=O)(=O)N(C)C)CC3)CC2=O)c(C)c1] | 1H NMR (400 MHz, Methanol-d4) δ = 1.77 (br t, J = 5.50 Hz, 4 H) 2.02-2.06 (m, 9 H) 2.49-2.65 (m, 4 H) 2.83 (s, 6 H) 3.33 (br d, J = 5.50 Hz, 4 H) 7.16 (s, 2 H). |
| A5 | 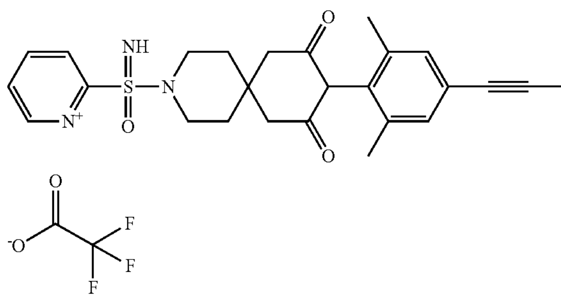 | 1H NMR (400 MHz, Methanol-d4/CDCl3 1:1) δ = 8.73 (br s, 1H), 8.13-7.97 (m, 2H), 7.62 (br s, 1H), 7.06 (s, 2H), 3.46-3.36 (m, 4H), 2.49 (s, 4H), 2.00 (s, 10H), 1.78 (br t, J = 5.3 Hz, 4H) |
| A6 | 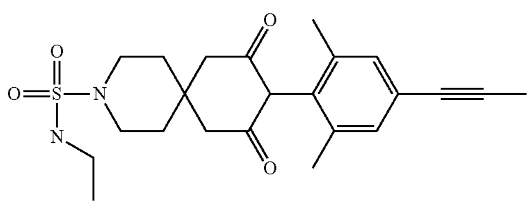 | 1H NMR (MeOD, 400 MHz): δ 7.03 (s, 2H), 3.23 (t, 4H), 3.04 (q, 2H), 2.58 (s, 4H), 2.0-1.99 (9H), 1.77 (t, 4H), 1.16 (t, 3H). |
| A7 | 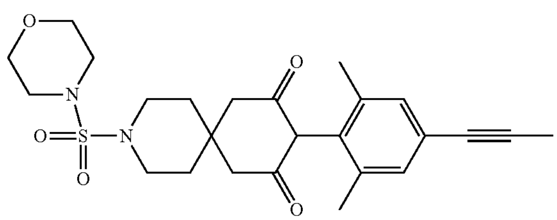 [SMILES: CC#Cc1cc(C)c(C2C(=O)CC3(CCN(S(=O)(=O)N4CCOCC4)CC3)CC2=O)c(C)c1] | 1H NMR (400 MHz, Methanol-d4) δ = 1.72-1.80(m, 4 H) 2.00-2.08 (m, 9 H) 2.55 (s, 4 H) 3.19-3.25 (m, 4 H) 3.31-3.39 (m, 4 H) 3.69-3.76 (m, 4 H) 7.15 (s, 2 H). |
| A8 | 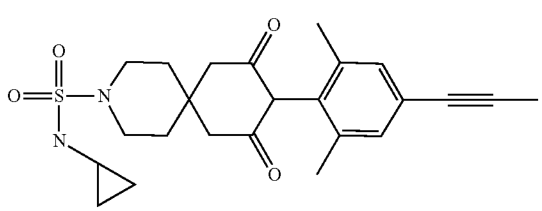 | 1H NMR (MeOD, 400 MHz): δ 7.03 (s, 2H), 3.30 (t, 4H), 2.59 (s, 4H), 2.46-2.43 (m, 1H), 2.0-1.99 (9H), 1.78 (t, 4H), 0.64-0.61 (m, 4H). |
| A9 | 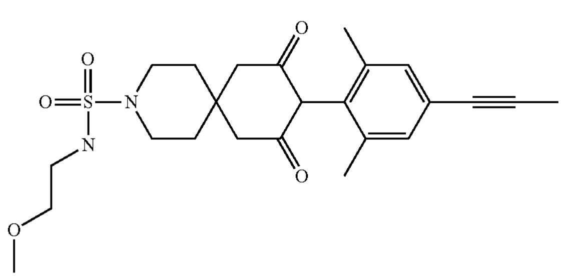 | 1H NMR (MeOD, 400 MHz): δ 7.02 (s, 2H), 3.47 (t, 2H), 3.36 (s, 3H), 3.24 (t, 4H), 3.17 (t, 2H), 2.57 (s, 4H), 2.0-1.99 (9H), 1.77 (t, 4H). |

TABLE 1-continued

| Compound | Structure | NMR |
|---|---|---|
| A10 | 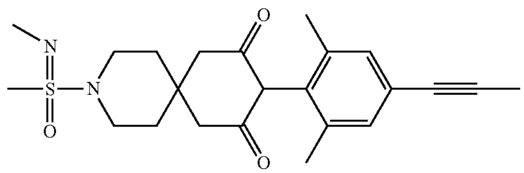 [SMILES: CC#Cc1cc(C)c(C2C(=O)CC3(CCN(S(C)(=O)=NC)CC3)CC2=O)c(C)c1] | 1H NMR (400 MHz, Methanol-d4) δ = 7.02 (s, 2H), 3.67 (s, 2H), 3.45-3.40 (m, 2H), 2.72 (s, 2H), 2.68 (s, 2H), 2.04-1.90 (m, 19H) |
| A11 | 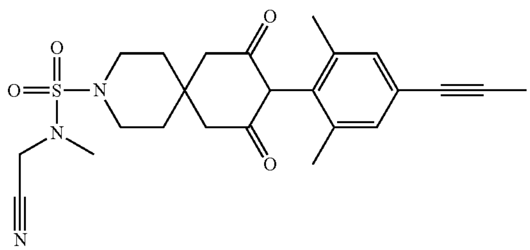 [SMILES: CC#Cc1cc(C)c(C2C(=O)CC3(CCN(S(=O)(=O)N(C)CC#N)CC3)CC2=O)c(C)c1] | 1H NMR (400 MHz, Methanol-d4) δ =7.01 (s, 2H), 4.26 (s, 2H), 3.34 (t, 4H), 2.95 (s, 3H), 2.54 (s, 4H), 2.0 (s, 6H), 1.98 (s, 3H), 1.78 (t, 4H). |
| A12 | 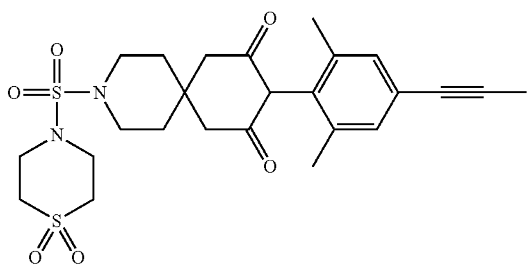 [SMILES: CC#Cc1cc(C)c(C2C(=O)CC3(CCN(S(=O)(=O)N4CCS(=O)(=O)CC4)CC3)CC2=O)c(C)c1] | 1H NMR (400 MHz, Methanol-d4) δ = 7.0 (s, 2H), 3.79 (t, 4H), 3.29 (4H, merged with MeOD), 3.18 (t, 4H), 2.49 (s, 4H), 2.0 (s, 6H), 1.98 (s, 3H), 1.76 (t, 4H) |
| A13 | 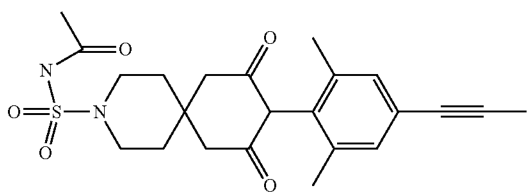 [SMILES: CC#Cc1cc(C)c(C2C(=O)CC3(CCN(S(=O)(=O)NC(C)=O)CC3)CC2=O)c(C)c1] | 1H NMR (400 MHz, Methanol-d4) δ = 1.72-1.84(m, 5 H) 1.96-2.08(m, 13 H) 2.56 (s, 4 H) 3.36-3.47 (m, 5 H) 7.03 (s, 2 H). |

TABLE 2

| Compound | Structure | NMR |
|---|---|---|
| P1 | 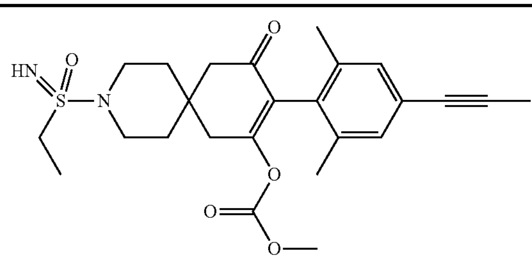 | 1H NMR (400 MHz, CDCl3) δ = 7.08 (s, 2H), 3.69 (s, 3H), 3.46-3.31 (m, 4H), 3.03 (d, J = 7.5 Hz, 1H), 2.99-2.88 (m, 1H), 2.76 (s, 2H), 2.65-2.57 (m, 2H), 2.03 (s, 3H), 2.02 (s, 6H), 1.89-1.70 (m, 4H), 1.41 (t, J = 7.5 Hz, 3H). |
| P2 | 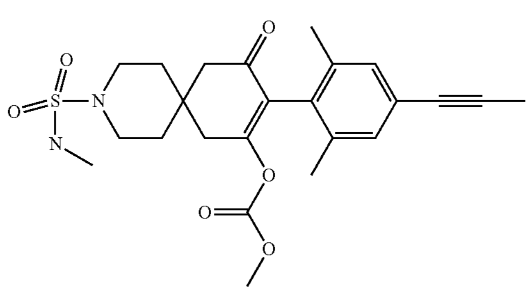 | 1H NMR (400 MHz, CDCl3) δ = 7.11-7.01 (m, 2H), 4.05-3.94 (m, 1H), 3.71-3.70 (m, 2H), 3.70-3.68 (m, 3H), 3.39-3.21 (m, 4H), 2.79-2.74 (m, 4H), 2.04-2.01 (m, 9H), 1.91-1.71 (m, 4H) |

TABLE 2-continued

| Compound | Structure | NMR |
|---|---|---|
| P3 | 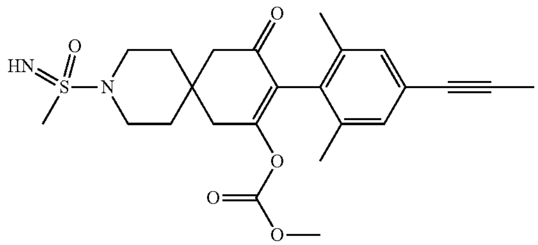 [SMILES: CC#Cc1cc(C)c(C2=C(OC(=O)OC)CC3(CCN(S(C)(=N)=O)CC3)CC2=O)c(C)c1] | 1H NMR (400 MHz, CDCl3) δ = 7.08 (s, 2H), 3.69 (s, 3H), 3.41-3.27 (m, 4H), 2.83 (s, 3H), 2.77 (s, 2H), 2.62 (s, 2H), 2.03 (m, 9H), 1.93-1.75 (m, 4H) |
| P4 | 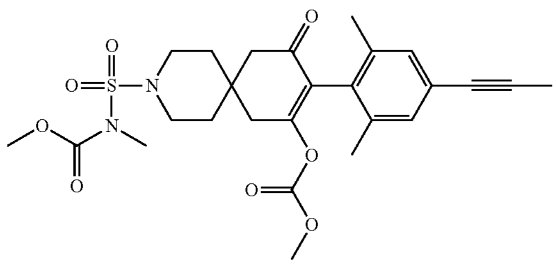 [SMILES: CC#Cc1cc(C)c(C2=C(OC(=O)OC)CC3(CCN(S(=O)(=O)N(C)C(=O)OC)CC3)CC2=O)c(C)c1] | $^1$H NMR (400 MHz, chloroform) δ = 7.12-7.05 (m, 2H), 3.86-3.78 (m, 3H), 3.74-3.64 (m, 3H), 3.48-3.39 (m, 4H), 3.31-3.22 (m, 3H), 2.79-2.73 (m, 2H), 2.64- 2.54 (m, 2H), 2.05-1.99 (m, 9H), 1.91-1.72 (m, 4H) |

Biological Examples

Seeds of a variety of test species are sown in standard soil in pots (*Lolium perenne* (LOLPE), *Setaria faberi* (SETFA), *Alopecurus myosuroides* (ALOMY), *Echinochloa crus-galli* (ECHCG), *Avena fatua* (AVEFA)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 250 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five-point scale (5=80-100%; 4=60-79%; 3=40-59%; 2=20-39%; 1=0-19%). NT=not tested.

TABLE B1

Application pre-emergence

| Compound | Rate (g/Ha) | ECHCG | SETFA | LOLPE | AVEFA | ALOMY |
|---|---|---|---|---|---|---|
| A1 | 250 | 5 | 5 | 5 | 5 | 5 |
| A2 | 250 | 5 | 5 | 5 | 5 | 5 |
| A3 | 250 | 5 | 5 | 5 | 5 | 5 |
| A4 | 250 | 5 | 5 | 5 | 5 | 5 |
| A5 | 250 | 5 | 5 | 5 | 5 | NT |
| A6 | 250 | 5 | 5 | 4 | 4 | 3 |
| A7 | 250 | 5 | 5 | 5 | 1 | 2 |
| A11 | 250 | 5 | 5 | 4 | 2 | 1 |
| A12 | 250 | 5 | 5 | 4 | 5 | 5 |
| A13 | 250 | 5 | 5 | 5 | 5 | 5 |
| P1 | 250 | 5 | 5 | 5 | 5 | 5 |
| P2 | 250 | 5 | 5 | 5 | 5 | 5 |
| P3 | 250 | 5 | 5 | 5 | 5 | 5 |
| P4 | 250 | 5 | 5 | 5 | 5 | 5 |

TABLE B2

Application post-emergence

| Compound | Rate (g/Ha) | LOLPE | AVEFA | ALOMY | ECHCG | SETFA |
|---|---|---|---|---|---|---|
| A1 | 250 | 5 | 5 | 5 | 5 | 5 |
| A2 | 250 | 5 | 5 | 5 | 5 | 5 |
| A3 | 250 | 5 | 5 | 5 | 5 | 5 |
| A4 | 250 | 5 | 5 | 5 | 5 | 5 |
| A5 | 250 | 5 | 5 | NT | 5 | 5 |
| A6 | 250 | 5 | 5 | 5 | 5 | 5 |
| A7 | 250 | 5 | 5 | 5 | 5 | 5 |
| A11 | 250 | 5 | 5 | 5 | 5 | 5 |
| A12 | 250 | 4 | 5 | 5 | 5 | 5 |
| A13 | 250 | 5 | 5 | 5 | 5 | 5 |
| P1 | 250 | 5 | 5 | 5 | 5 | 5 |
| P2 | 250 | 5 | 5 | 5 | 5 | 5 |
| P3 | 250 | 5 | 5 | 5 | NT | 5 |
| P4 | 250 | 5 | 5 | 5 | 5 | 5 |

Comparison

Using procedures outlines above, wheat and barley crop plants are treated, post-emergence with compounds A1 or A3 of the present invention or comparator compound $C_1$ (Compound A-38 from WO2014/096289) at the application rates indicated. The compounds were also applied in conjunction with the safener compound cloquintocet-mexyl (CQC) at 50 g/ha.

TABLE B3

| Compound | Rate g/ha | Wheat | Barley |
|---|---|---|---|
| A1 | 30 | 0 | 0 |
| | 60 | 0 | 0 |
| | 60 + CQC | 0 | — |
| A3 | 30 | 0 | 0 |
| | 60 | 0 | 0 |
| | 60 + CQC | 0 | — |
| C1 | 30 | 40 | 80 |
| | 60 | 70 | 90 |
| | 60 + CQC | 60 | — |

The results outlined in Table B3 above show % phytotoxicity observed and that compounds A1 and A3 of the present invention is significantly less damaging to the wheat and barley crops compared to prior art compound C1.

| Compound | Structure |
|---|---|
| C1 (Compound A-38 from WO2014/096289) | 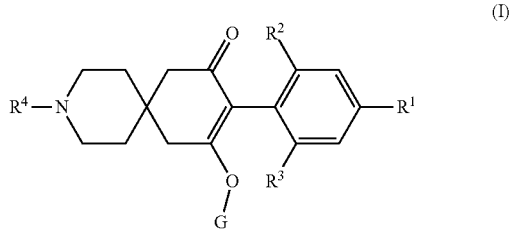 |

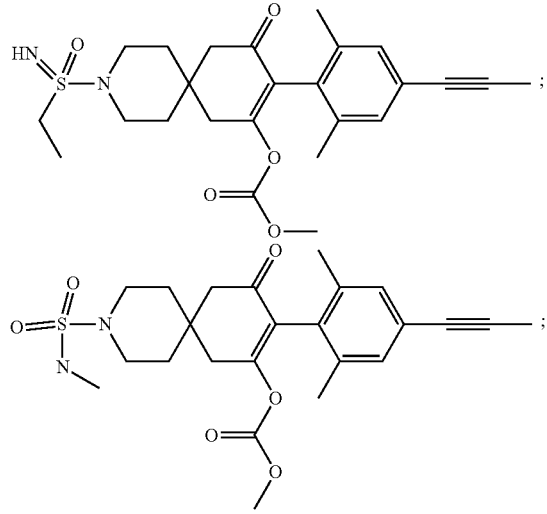

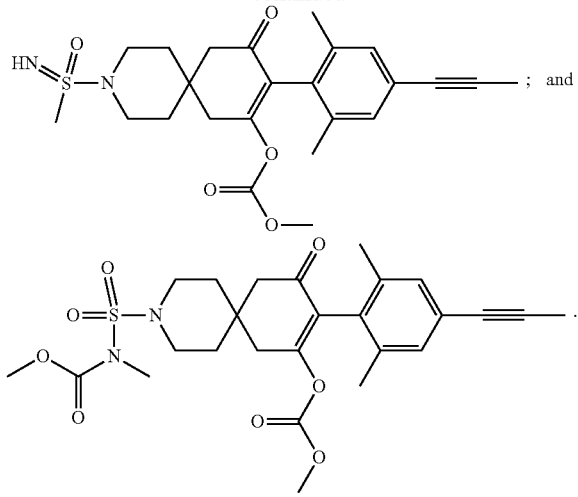
16. A compound, or an agriculturally acceptable salt thereof, selected from the group consisting of:
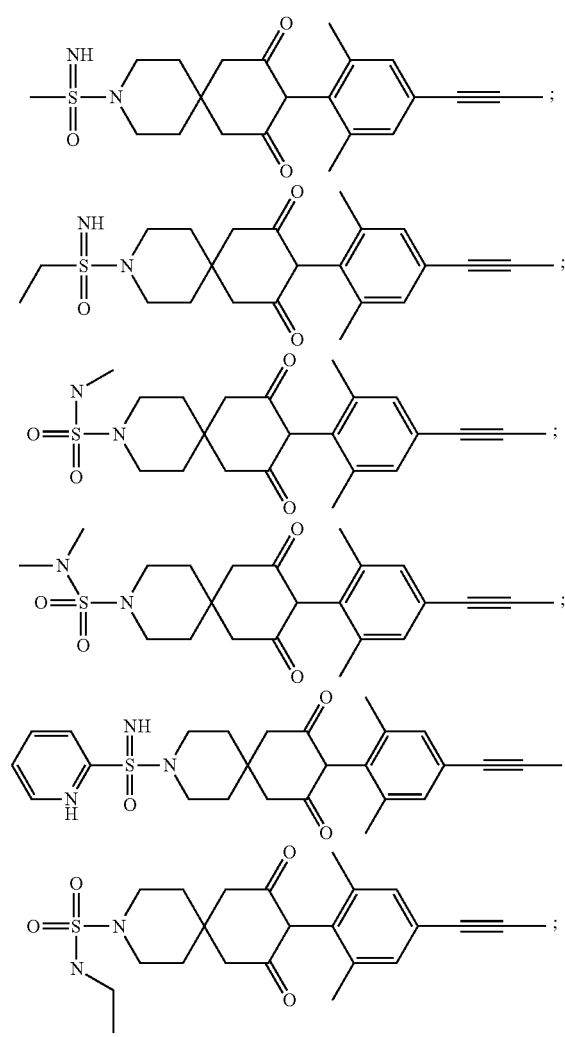
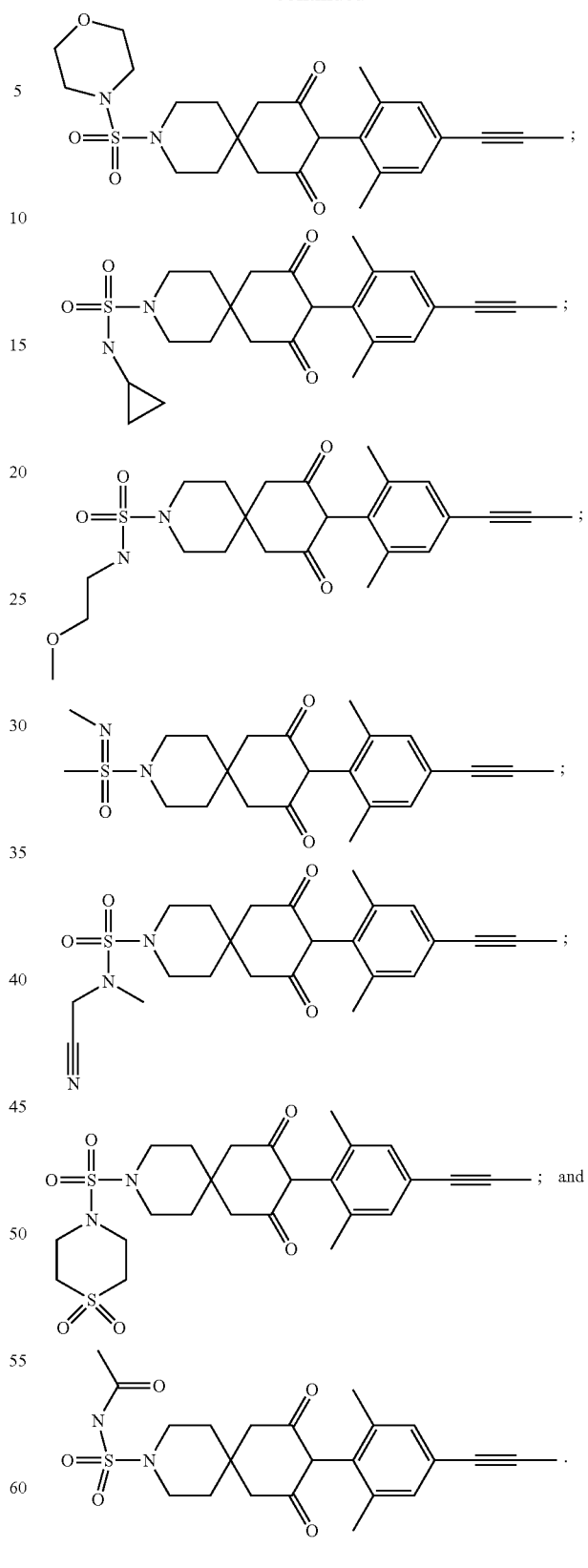

The invention claimed is:

1. A compound of Formula (I)

$$\text{(I)}$$

wherein
R$^1$ is selected from the group consisting of methyl, ethynyl, 1-propynyl, phenyl and a 5 or 6 membered heteroaryl which comprises one or two nitrogen heteroatoms, said phenyl and heteroaryl optionally substituted by one or two R$^9$ substituents;
R$^2$ is selected from the group consisting of methyl, ethyl, methoxy and chloro;
R$^3$ is selected from the group consisting of methyl, ethyl, methoxy and chloro;
R$^4$ is —S(O)$_2$NR$^5$R$^6$ or —S(O)(=NR$^7$)R$^8$;
R$^5$ is hydrogen or C$_1$-C$_6$alkyl; and
R$^6$ is selected from the group consisting of hydrogen, C$_1$-C$_6$alkyl, C$_3$-C$_6$cycloalkyl, C$_1$-C$_6$ alkoxy-C$_1$-C$_3$alkyl-, —C(O)C$_1$-C$_6$alkyl, —C(O)OC$_1$-C$_6$alkyl and CH$_2$CN; or
R$^5$ and R$^6$ together form —CH$_2$CH$_2$OCH$_2$CH$_2$—, —CH$_2$CH$_2$S(O)$_2$CH$_2$CH$_2$—; and
R$^7$ is hydrogen or C$_1$-C$_6$alkyl;
R$^8$ is selected from the group consisting of hydrogen, C$_1$-C$_6$ alkyl, C$_1$-C$_6$ alkoxy, C$_3$-C$_6$cycloalkyl, phenyl,-pyridyl, wherein the phenyl and pyridyl are optionally substituted by one, two or three substituents independently selected from the group consisting of C$_1$-C$_3$alkyl, C$_1$-C$_3$haloalkyl, C$_1$-C$_3$alkoxy, C$_2$-C$_3$alkenyl, C$_2$-C$_3$alkynyl, halogen, cyano and nitro;
R$^9$ is independently selected from the group consisting of C$_1$-C$_4$ alkyl, C$_1$-C$_4$ haloalkyl, cyano and halogen;
G is selected from the group consisting of hydrogen, —(CH$_2$)$_n$—R$^a$, —C(O)—R$^a$, —C(O)—(CR$^c$R$^d$)$_n$—O—R$^b$, —C(O)—(CR$^c$R$^d$)$_n$—S—R$^b$, —C(O)NR$^a$R$^a$, —S(O)$_2$—R$^a$ and C$_1$-C$_8$alkoxy-C$_1$-C$_3$alkyl-;
R$^a$ is independently selected from the group consisting of hydrogen, C$_1$-C$_8$alkyl, C$_1$-C$_3$haloalkyl, C$_2$-C$_8$alkenyl, C$_2$-C$_8$alkynyl, C$_3$-C$_6$cycloalkyl, heterocyclyl and phenyl wherein said heterocyclyl and phenyl groups are optionally substituted by one, two or three substituents independently selected from the group consisting of C$_1$-C$_3$alkyl, C$_1$-C$_3$haloalkyl, C$_1$-C$_3$alkoxy, C$_2$-C$_3$alkenyl, C$_2$-C$_3$alkynyl, halogen, cyano and nitro;
R$^b$ is selected from the group consisting of C$_1$-C$_8$alkyl, C$_1$-C$_3$haloalkyl, C$_2$-C$_8$alkenyl, C$_2$-C$_8$alkynyl, C$_3$-C$_6$ cycloalkyl, heterocyclyl and phenyl wherein said heterocyclyl and phenyl groups are optionally substituted by one, two or three substituents independently selected from the group consisting of C$_1$-C$_3$alkyl, C$_1$-C$_3$haloalkyl, C$_1$-C$_3$alkoxy, C$_2$-C$_3$alkenyl, C$_2$-C$_3$alkynyl, halogen, cyano and nitro;
R$^c$ is hydrogen or C$_1$-C$_3$ alkyl;
R$^d$ is hydrogen or C$_1$-C$_3$ alkyl; and
n is independently 0, 1 or 2;
or an agriculturally acceptable salt thereof.

2. The compound of according to claim 1, wherein R$^1$ is 1-propynyl, R$^2$ is methyl or methoxy and R$^3$ is methyl or methoxy.

3. The compound according to claim 1, wherein R$^2$ is methyl.

4. The compound according to claim 1, wherein R$^3$ is methyl.

5. The compound according to claim 1, wherein R$^3$ is methoxy.

6. The compound according to claim 1, wherein R$^4$ is —S(O)$_2$NR$^5$R$^6$.

7. The compound according to claim 1, wherein R$^4$ is —S(O)(=NR$^7$)R$^8$.

8. The compound according to claim 1, wherein G is hydrogen.

9. The compound according to claim 1, wherein G is —C(O)C$_1$-C$_6$alkyl.

10. The compound according to claim 1, wherein G is —C(O)—O—C$_1$-C$_6$alkyl.

11. A herbicidal composition comprising the compound of Formula (I) according to claim 1 and an agriculturally acceptable formulation adjuvant.

12. The herbicidal composition according to claim 11, further comprising at least one additional pesticide.

13. The herbicidal composition according to claim 12, wherein the additional pesticide is a herbicide or herbicide safener.

14. A method of controlling weeds, at a locus comprising applying to the locus of the weeds a weed controlling amount of the composition according to claim 11.

15. A compound, or an agriculturally acceptable salt thereof, selected from the group consisting of: